(12) United States Patent
Bamber et al.

(10) Patent No.: US 10,857,568 B2
(45) Date of Patent: Dec. 8, 2020

(54) EXTRACTING MINED ORE, MINERALS OR OTHER MATERIALS USING SENSOR-BASED SORTING

(71) Applicant: MineSense Technologies Ltd., Vancouver (CA)

(72) Inventors: Andrew Sherliker Bamber, Vancouver (CA); Darcy James Houlahan, Vancouver (CA)

(73) Assignee: MineSense Technologies Ltd., Vancouver (CA)

(*) Notice: Subject to any disclaimer, the term of this patent is extended or adjusted under 35 U.S.C. 154(b) by 0 days.

(21) Appl. No.: 16/027,612

(22) Filed: Jul. 5, 2018

(65) Prior Publication Data
US 2019/0137424 A1    May 9, 2019

Related U.S. Application Data

(63) Continuation of application No. 15/833,925, filed on Dec. 6, 2017, now Pat. No. 10,054,560, which is a
(Continued)

(51) Int. Cl.
*B07C 5/344* (2006.01)
*E02F 7/06* (2006.01)
(Continued)

(52) U.S. Cl.
CPC .............. *B07C 5/344* (2013.01); *B02C 23/08* (2013.01); *B07C 5/00* (2013.01); *E02F 3/28* (2013.01);
(Continued)

(58) Field of Classification Search
CPC .... G01N 27/025; G01N 231/12; G01N 33/24; B02C 23/08; E02F 3/28; E02F 3/40; E02F 7/06; E02F 9/26; E02F 9/265
(Continued)

(56) References Cited

U.S. PATENT DOCUMENTS 719,343 A    1/1903   Langerfeld
3,209,910 A  10/1965  Palmer
(Continued)

FOREIGN PATENT DOCUMENTS

AU    2006249259 A1    6/2007
CA       2629408 A1   11/2009
(Continued)

OTHER PUBLICATIONS

Examination Report for European Patent Application No. 15824911.0, dated Jul. 18, 2019, 5 pages.
(Continued)

*Primary Examiner* — Terrell H Matthews
(74) *Attorney, Agent, or Firm* — Perkins Coie LLP

(57) ABSTRACT

A method of analyzing minerals received within a mining shovel bucket includes collecting data associated with ore received in the bucket, where the bucket includes at least one active sensor, where the ore includes one or more mineral, and where the ore is within a field of the active sensor. The method further includes determining a content of the minerals using the data, transmitting information relating to the content of the minerals to a decision support system, and sorting or processing the ore based on an output of the decision support system. Collecting data associated with the ores may include generating source signals, applying the source signals to the active sensor, collecting a response from the active sensor, and comparing the response with a reference or threshold. Other features are disclosed.

11 Claims, 12 Drawing Sheets

Related U.S. Application Data continuation of application No. 15/040,991, filed on Feb. 10, 2016, now Pat. No. 9,958,407, which is a continuation of application No. 14/584,654, filed on Dec. 29, 2014, now Pat. No. 9,290,913, which is a continuation of application No. 13/538,931, filed on Jun. 29, 2012, now Pat. No. 8,958,905.

(60) Provisional application No. 61/502,760, filed on Jun. 29, 2011, provisional application No. 61/502,772, filed on Jun. 29, 2011.

(51) Int. Cl.
| | |
|---|---|
| *E02F 9/26* | (2006.01) |
| *G01N 33/24* | (2006.01) |
| *B02C 23/08* | (2006.01) |
| *B07C 5/00* | (2006.01) |
| *E02F 3/28* | (2006.01) |
| *E02F 3/40* | (2006.01) |
| *G01N 27/02* | (2006.01) |

(52) U.S. Cl.
CPC .............. *E02F 3/40* (2013.01); *E02F 7/06* (2013.01); *E02F 9/26* (2013.01); *E02F 9/265* (2013.01); *G01N 27/025* (2013.01); *G01N 33/24* (2013.01)

(58) Field of Classification Search
USPC ........................................................ 209/571
See application file for complete search history.

(56) References Cited

U.S. PATENT DOCUMENTS

| | | | |
|---|---|---|---|
| 3,263,160 A | 7/1966 | Dolan et al. | |
| 3,337,328 A | 8/1967 | Lawver | |
| 3,655,964 A | 4/1972 | Slight | |
| 3,701,419 A * | 10/1972 | Hutter | B07C 5/366 |
| | | | 209/570 |
| 3,747,755 A | 7/1973 | Senturia et al. | |
| 4,006,481 A | 2/1977 | Young et al. | |
| 4,030,026 A | 6/1977 | Payne | |
| 4,128,803 A | 12/1978 | Payne | |
| 4,236,640 A | 12/1980 | Knight | |
| 4,241,835 A | 12/1980 | Lockett | |
| 4,300,097 A | 11/1981 | Turner | |
| 4,361,238 A | 11/1982 | Kealy et al. | |
| 4,365,719 A | 12/1982 | Kelly | |
| 4,441,616 A * | 4/1984 | Konig | B07C 5/36 |
| | | | 209/44.1 |
| 4,507,612 A | 3/1985 | Payne | |
| 4,600,356 A | 7/1986 | Bridges et al. | |
| 4,659,989 A | 4/1987 | Kerr | |
| 4,909,930 A | 3/1990 | Cole | |
| 5,197,607 A | 3/1993 | Hakansson | |
| 5,236,092 A | 8/1993 | Krotkov | |
| 5,285,972 A | 2/1994 | Notebaart | |
| 5,413,222 A * | 5/1995 | Holder | B07C 5/344 |
| | | | 209/567 |
| 5,523,690 A | 6/1996 | Rowan | |
| 5,592,092 A | 1/1997 | Mechler | |
| 5,813,543 A | 9/1998 | Gesing et al. | |
| RE36,537 E | 2/2000 | Sommer et al. | |
| 6,078,018 A | 6/2000 | Davis et al. | |
| 6,444,936 B1 | 9/2002 | Ludwig et al. | |
| 6,545,240 B2 | 4/2003 | Kumar | |
| 6,664,914 B2 | 12/2003 | Longstaff et al. | |
| 6,693,274 B2 * | 2/2004 | Baird | B07C 5/06 |
| | | | 156/360 |
| 6,753,957 B1 | 6/2004 | Graft et al. | |
| 6,817,474 B2 * | 11/2004 | Ikeda | B03C 1/14 |
| | | | 209/223.2 |
| 7,161,672 B2 | 1/2007 | Gronushkin et al. | |
| 7,564,943 B2 | 7/2009 | Sommer et al. | |
| 7,574,821 B2 | 8/2009 | Furem | |
| 7,595,489 B2 | 9/2009 | Statham | |
| 7,737,379 B2 | 6/2010 | Witdouck | |
| 7,763,820 B1 | 7/2010 | Sommer et al. | |
| 7,786,401 B2 | 8/2010 | Valerio | |
| 7,797,861 B2 | 9/2010 | Wright | |
| 7,909,169 B1 | 3/2011 | Slade | |
| 7,948,237 B2 | 5/2011 | Kuzmin et al. | |
| 7,965,167 B2 | 6/2011 | Volker et al. | |
| 7,970,574 B2 | 6/2011 | Jin | |
| 8,100,581 B2 | 1/2012 | Djordjevic | |
| 8,138,437 B2 | 3/2012 | Valerio | |
| 8,315,838 B2 | 11/2012 | Durrant-Whyte | |
| 8,446,156 B2 | 5/2013 | Morrison | |
| 8,515,008 B2 | 8/2013 | Ulberg et al. | |
| 8,600,545 B2 | 12/2013 | Earlam | |
| 8,664,595 B2 | 3/2014 | Buhot et al. | |
| 8,766,129 B2 | 7/2014 | Kazakov et al. | |
| 8,812,149 B2 | 8/2014 | Doak | |
| 8,820,533 B2 | 9/2014 | Shaw et al. | |
| 8,843,266 B2 | 9/2014 | Lindskov | |
| 8,855,809 B2 * | 10/2014 | Spencer | B07C 5/3416 |
| | | | 378/53 |
| 8,875,901 B2 | 11/2014 | Wellwood et al. | |
| 8,908,829 B2 | 12/2014 | Watanabe et al. | |
| 8,931,720 B2 | 1/2015 | Box et al. | |
| 8,937,282 B2 | 1/2015 | Owen et al. | |
| 8,957,340 B2 | 2/2015 | Wellwood et al. | |
| 8,958,905 B2 | 2/2015 | Bamber et al. | |
| 9,010,543 B2 | 4/2015 | Box et al. | |
| 9,114,433 B2 | 8/2015 | Roos et al. | |
| 9,290,913 B2 | 3/2016 | Bamber et al. | |
| 9,314,823 B2 | 4/2016 | Bamber et al. | |
| 9,316,537 B2 | 4/2016 | Bamber et al. | |
| 9,764,361 B2 | 9/2017 | Valerio | |
| 9,958,407 B2 | 5/2018 | Bamber et al. | |
| 10,029,284 B2 | 7/2018 | Bamber et al. | |
| 10,054,560 B2 | 8/2018 | Bamber et al. | |
| 2003/0009286 A1 | 1/2003 | Shibusawa | |
| 2004/0066890 A1 | 4/2004 | Dalmijn et al. | |
| 2005/0002029 A1 | 1/2005 | Gornushkin et al. | |
| 2005/0150844 A1 | 7/2005 | Hyndman | |
| 2005/0242006 A1 | 11/2005 | Bohlig | |
| 2006/0090379 A1 | 5/2006 | Furem | |
| 2006/0171504 A1 | 8/2006 | Sommer et al. | |
| 2007/0030953 A1 | 2/2007 | Sommer et al. | |
| 2008/0047170 A1 | 2/2008 | Nichols | |
| 2008/0192987 A1 | 8/2008 | Helgason et al. | |
| 2009/0076674 A1 | 3/2009 | Kiegeral et al. | |
| 2009/0322357 A1 * | 12/2009 | Beaulieu | G01V 3/088 |
| | | | 324/692 |
| 2010/0005926 A1 | 1/2010 | Valerio | |
| 2010/0091103 A1 | 4/2010 | Peltonen et al. | |
| 2011/0066404 A1 | 3/2011 | Salazar-Tio et al. | |
| 2011/0186660 A1 | 8/2011 | Harding et al. | |
| 2011/0313625 A1 | 12/2011 | Miller et al. | |
| 2012/0033212 A1 | 2/2012 | Barefield | |
| 2012/0046983 A1 | 2/2012 | Nettleton et al. | |
| 2012/0148018 A1 | 6/2012 | Sommer, Jr. | |
| 2013/0026263 A1 | 1/2013 | Bamber et al. | |
| 2013/0098807 A1 | 4/2013 | Wellwood et al. | |
| 2013/0126399 A1 | 5/2013 | Wolff | |
| 2013/0169961 A1 | 7/2013 | Kraft | |
| 2013/0201481 A1 | 8/2013 | Bamber et al. | |
| 2013/0272829 A1 | 11/2013 | Innes et al. | |
| 2013/0292307 A1 | 11/2013 | Bamber et al. | |
| 2013/0313169 A1 | 11/2013 | Lapeyre et al. | |
| 2014/0088876 A1 | 3/2014 | Shiley et al. | |
| 2014/0144342 A1 | 5/2014 | Bye | |
| 2014/0200054 A1 | 7/2014 | Fraden | |
| 2014/0225416 A1 | 8/2014 | Harding et al. | |
| 2014/0260801 A1 | 9/2014 | Wellwood et al. | |
| 2015/0004574 A1 | 1/2015 | Bomer | |
| 2015/0085123 A1 | 3/2015 | Tafazoli | |
| 2015/0108258 A1 | 4/2015 | Bamber et al. | |
| 2016/0016203 A1 | 1/2016 | Bamber et al. | |
| 2016/0054044 A1 | 2/2016 | Jeong et al. | |
| 2016/0107197 A1 | 4/2016 | Hartmann | |

(56) References Cited

U.S. PATENT DOCUMENTS

| | | | |
|---|---|---|---|
| 2016/0299116 A1 | 10/2016 | Talmaki | |
| 2017/0028443 A1 | 2/2017 | Bamber et al. | |
| 2017/0037594 A1 | 2/2017 | Wada | |
| 2017/0121945 A1 | 5/2017 | Bamber et al. | |
| 2019/0001374 A1 | 1/2019 | Bamber et al. | |
| 2020/0123732 A1 | 4/2020 | Hall et al. | |
| 2020/0139406 A1 | 5/2020 | Bamber et al. | |

FOREIGN PATENT DOCUMENTS

| | | | | |
|---|---|---|---|---|
| CA | 2840545 A1 | 1/2013 | | |
| DE | 3228447 | 4/1986 | | |
| EP | 2141414 | 1/2010 | | |
| JP | S5389701 | 7/1978 | | |
| JP | H0742201 | 2/1995 | | |
| WO | 9530880 A1 | 11/1995 | | |
| WO | WO-9530880 A1 * | 11/1995 | ............. | E02F 9/205 |
| WO | 9922870 A1 | 5/1999 | | |
| WO | 2005085968 A1 | 9/2005 | | |
| WO | WO-2005085968 A1 * | 9/2005 | ........... | E01C 19/004 |
| WO | 2008046136 A1 | 4/2008 | | |
| WO | 2008129115 A1 | 10/2008 | | |
| WO | 2009076674 A1 | 6/2009 | | |
| WO | 2010028446 A1 | 3/2010 | | |
| WO | 2011116417 A1 | 9/2011 | | |
| WO | 2011120086 A1 | 10/2011 | | |
| WO | 2011134009 A1 | 11/2011 | | |
| WO | 2011150464 A1 | 12/2011 | | |
| WO | 2013001364 A2 | 1/2013 | | |
| WO | WO-2013001364 A2 * | 1/2013 | ............... | E02F 9/26 |
| WO | 2013016774 A1 | 2/2013 | | |
| WO | 2013033572 | 3/2013 | | |
| WO | WO-2013033572 A2 * | 3/2013 | ............ | B07C 5/346 |
| WO | 2013163756 A1 | 11/2013 | | |
| WO | 2016008059 A1 | 1/2016 | | |

OTHER PUBLICATIONS

Examination Report for European Patent Application No. 12803664.7, dated Apr. 8, 2019, 7 pages.
Examination Report for European Patent Application No. 13784189.6, dated Apr. 23, 2019, 3 pages.
Examination Report for Australian Patent Application No. 2018203576, dated Jul. 30, 2019, 7 pages.
Examination Report for Australian Patent Application No. 2018204838, dated Aug. 8, 2019, 4 pages.
Bamber, Andrew Sherliker, "Integrated Mining, Pre-Construction and Waste Disposal Systems for the Increased Sustainability of Hard Rock Metal Mining," Apr. 2008, pp. 29, 37-44, 85-89. <https://circle.ubc.ca/handle/2429/779>.
Examination Report for Australian Patent Application 2012277493; dated Jul. 8, 2016, 4 pages.
Examination Report for Australian Patent Application 2013255048; dated Jan. 21, 2016, 3 pages.
Examination Report for Australian Patent Application 2017201320; dated Mar. 28, 2018, 4 pages.
Examination Report for Australian Patent Application 2013255051; dated Jan. 27, 2016, 3 pages.
Examination Report for Australian Patent Application No. 2015292229, dated Apr. 3, 2018, 6 pages.
Examination Report for Australian Patent Application No. 2015292228, dated Oct. 4, 2017, 4 pages.
Examination Report for Australian Patent Application No. 2015292229, dated Oct. 13, 2017, 4 pages.
Examination Report for Australian Patent Application No. 2016216528, dated Nov. 2, 2017, 5 pages.
Examination Report for Australian Patent Application No. 2017202941, dated Jan. 12, 2018, 2 pages.
Examination Report for Canadian Patent Application 2,840,545; dated Mar. 23, 2016, 3 pages.
Examination Report for European Patent Application No. 13784899.0, dated Jun. 20, 2017, 3 pages.
Extended European Search Report for European Application No. 12803664.7; dated Feb. 10, 2016, 17 pages.
Extended European Search Report for European Application No. 13784189.6; dated Nov. 5, 2015, 7 pages.
Extended European Search Report for European Application No. 13784899.0; dated Jun. 10, 2016, 11 pages.
Extended European Search Report for European Application No. 15824911.0, dated Jan. 31, 2018, 10 pages.
Extended European Search Report for European Patent Application No. 15824840.1, dated Mar. 8, 2018, 5 pages.
Extended European Search Report for European Patent Application No. 18166364.2, dated Jul. 10, 2018, 6 pages.
First Official Action in Chilean Patent Application 2924-2014, dated Oct. 29, 2014, 5 pages.
First Official Action in Chilean Patent Application 2925-2014, dated Oct. 29, 2014, 5 pages.
First Office Action in Chinese Patent Application 201580050856.21; dated May 3, 2018, 23 pages, with English translation.
First Office Action in Chinese Patent Application 201580050857.7; dated Dec. 5, 2018, 9 pages, with English translation.
First Office Action in Chilean Patent Application No. 2017-00150; dated Jun. 20, 2018, 7 pages.
International Search Report and Written Opinion for International Application No. PCT/CA2013/050330, dated Jul. 24, 2013, 9 pages.
International Search Report and Written Opinion for International Application No. PCT/CA2013/050336, dated Aug. 12, 2013, 12 pages.
International Search Report and Written Opinion for International Application No. PCT/CA2015/050683; dated Oct. 21, 2015, 7 pages.
International Search Report and Written Opinion for International Application No. PCT/CA2015/050684, dated Sep. 30, 2015, 9 pages.
International Search Report and Written Opinion for International Application No. PCT/IB2012/001560, dated Nov. 29, 2012, 12 pages.
Kieba et al. "Differential Soil Impedance Obstacle Detection," U.S. Department of Energy Technical Report No. DE-FC26-02NT41318, Report Issue Date Jan. 17, 2005, 72 pages.
N. G. Cutmore et al., "Ore Characterisation and Sorting," Minerals Engineering, vol. 10, No. 4., Jan. 1997, 6 pages.
Office Action in Chile Patent Application No. 00164-2017, dated Apr. 5, 2018, 12 pages.
Office Action in Chile Patent Application No. 00164-2017, dated Sep. 12, 2018, 15 pages.
Partial Supplementary European Search Report for European Application No. 12803664.7, dated Oct. 16, 2015, 7 pages.
Partial Supplementary European Search Report for European Application No. 13784899.0, dated Feb. 16, 2016, 7 pages.
Second Examination Report for Australian Patent Application 2012277493, dated Sep. 27, 2016, 4 pages.
Second Office Action for Chilean Patent Application No. 2924-2014, dated Jan. 7, 2017, 5 pages.
Second Office Action for Chilean Patent Application No. 2925-2014, dated Feb. 25, 2017, 5 pages.
Second Office Action in Chilean Patent Application No. 2017-00150; dated Feb. 13, 2019, 7 pages.
Second Examination Report for Australian Patent Application No. 201592228, dated Feb. 28, 2018, 4 pages.
Singh et al., "Application of image processing and radial basis neural network techniques for ore sorting and ore classification," Minerals Engineering, vol. 18, Jan. 2005, 9 pages.
Supplementary European Search Report for European Application No. 12803664.7 dated Feb. 10, 2016, 11 pages.
Supplementary European Search Report for European Application No. 13784899.0; dated Feb. 16, 2016, 7 pages.
Third Examination Report for Australian Patent Application 2012277493; dated Mar. 3, 2017, 4 pages.
Yang et al., "Electromagnetic conductivities of rock cores: Theory and analog results," Geophysics, vol. 62, No. 6, Nov.-Dec. 1997, 15 pages.

(56) References Cited

OTHER PUBLICATIONS

U.S. Appl. No. 16/018,335 for Bamber et al., filed Jun. 26, 2018.
U.S. Appl. No. 16/028,222 for Bamber et al., filed Jul. 5, 2018.
U.S. Appl. No. 16/287,596 for Bamber et al., filed Feb. 27, 2019.
Examination Report for Australian Patent Application No. 2019204043, dated May 17, 2020, 5 pages.
Extended European Search Report for European Application No. 20165382.1; dated Jul. 27, 2020, 9 pages.
Second Office Action in Chinese Patent Application 201580050857.7; dated Jul. 31, 2019, 8 pages.
Third Office Action in Chinese Patent Application 201580050857.7; dated May 29, 2020, 4 pages.

* cited by examiner

EXTRACTING MINED ORE, MINERALS OR OTHER MATERIALS USING SENSOR-BASED SORTING

CROSS-REFERENCE TO RELATED APPLICATION(S)

This application is a continuation of U.S. Non-provisional application Ser. No. 15/833,925 filed on Dec. 6, 2017, entitled EXTRACTING MINED ORE, MINERALS OR OTHER MATERIALS USING SENSOR-BASED SORTING, which is a continuation of U.S. Non-provisional application Ser. No. 15/040,991 filed on Feb. 10, 2016, entitled Extracting Mined Ore, Minerals or Other Materials Using Sensor-Based Sorting, which is a continuation of U.S. Non-provisional application Ser. No. 14/584,654, filed on Dec. 29, 2014, entitled Extracting Mined Ore, Minerals Or Other Materials Using Sensor-Based Sorting, which is a continuation of U.S. Non-provisional application Ser. No. 13/538,931, filed on Jun. 29, 2012, entitled Extracting Mined Ore, Minerals Or Other Materials Using Sensor-Based Sorting, which claims the benefit of U.S. Provisional Application No. 61/502,760, filed on Jun. 29, 2011, entitled High Frequency Electromagnetic Spectrometer and U.S. Provisional Application No. 61/502,772, filed on Jun. 29, 2011, entitled Method for the Pre-concentration of Mineral Ores, which are all hereby incorporated by reference for all purposes in their entirety.

BACKGROUND

After materials are mined from the ground, portions of the material that have no beneficial use or value are typically separated or extracted from the portions that have beneficial use or value.

In the extraction of the valuable fractions from value-bearing mineral ores, the first step in beneficiation is generally comminution to fine particle sizes prior to extraction of the fine valuable fractions from the gangue material by means of froth flotation or lixiviation, for example. An alternative treatment, prior to conventional methods described, is ore sorting, where gangue material is detected by means of electronic sensors and removed from the value-bearing mineral ore at coarse particle sizes by physical means. Currently, there are various methods of sorting ore. In some examples, valuable fractions may be recovered from the ore stream by means of electronic sensors. In practice, this method results in unacceptable loss of valuable fractions due to lack of sensitivity in current electronic sensors. Furthermore, low capacity of these sorters unacceptably reduces the rate at which the valuable material can be extracted and processed.

Figure 1:
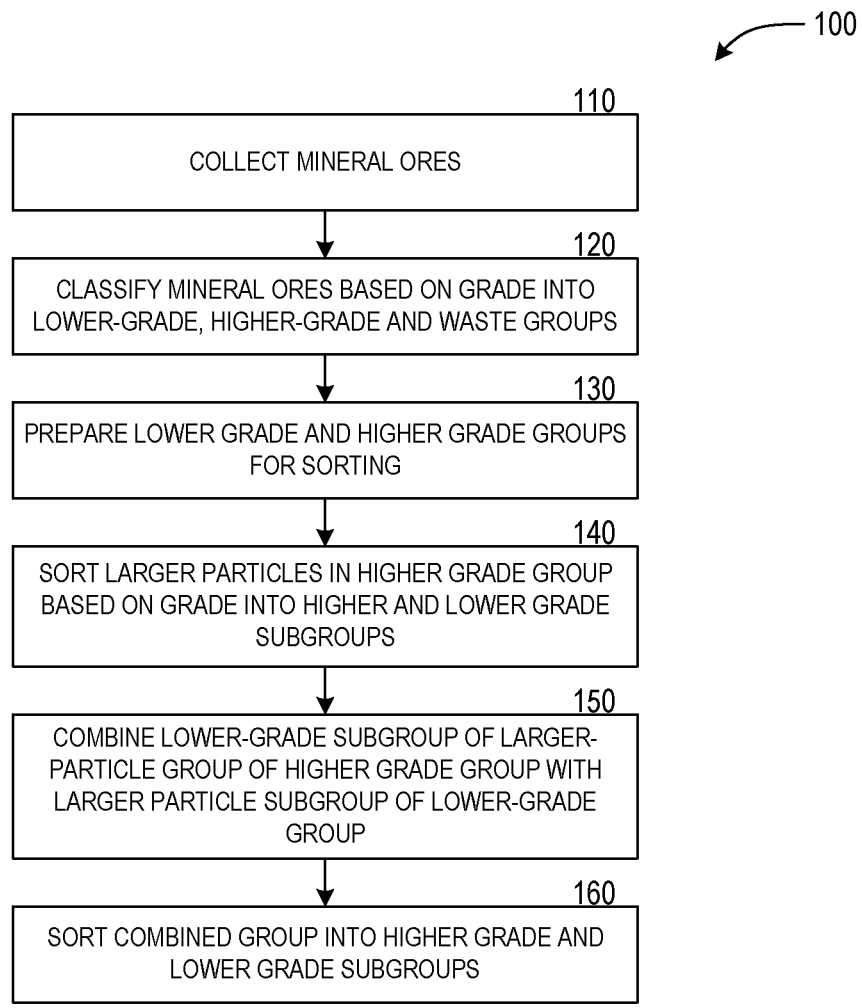
FIG. 1 illustrates a method of extracting materials.

The drawings have not necessarily been drawn to scale. For example, the dimensions of some of the elements in the figures may be expanded or reduced to help improve the understanding of the embodiments of the present invention. Similarly, some components and/or operations may be separated into different blocks or combined into a single block for the purposes of discussion of some of the embodiments of the present invention. Moreover, while the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the present invention generally relate to extracting materials, particularly mineral ores. More specifically, various embodiments of the present application relate to extracting materials using sensor-based sorting. More particularly, methods and systems for increasing the value and reducing the mass of material delivered to the beneficiation process through the application of sensor-based sorting are described. In some embodiments, the materials are minerals and mineral ores; however, embodiments of the present invention may be used in sorting other materials.

The minerals are extracted by using sensor-based methods and systems, which may be applied to large quantities of high-value or low-value ore, and achieve a high degree of value recovery at a high throughput and low cost. The methods and systems include various stages of sorting. In some embodiments, the sorting process uses electromagnetic sensing by induced potential, specifically for the evaluation of the conductive and/or magnetic content in the mineral samples. The sensors may be arbitrarily scaled and oriented, allowing the sensors to be coupled to shovels and other types of mining equipment. Using the methods and systems described, reports relating to the minerals, such as the content or quality of the mineral ore, can be generated very rapidly, for instance, at millisecond intervals or faster. Additionally, the systems and methods allow for high levels of discrimination (e.g., 0.05% in Nickel (Ni) and 0.1% in Copper (Cu)) and accuracy (e.g., of the order of 0.05% for Cu and Ni).

Various examples of the invention will now be described. The following description provides certain specific details for a thorough understanding and enabling description of these examples. One skilled in the relevant technology will understand, however, that the invention may be practiced without many of these details. Likewise, one skilled in the relevant technology will also understand that the invention may include many other obvious features not described in detail herein. Additionally, some well-known structures or functions may not be shown or described in detail below, to avoid unnecessarily obscuring the relevant descriptions of the various examples.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

Method of Extracting Materials

FIG. 1 illustrates a method 100 of extracting materials, such as mineral ores. In some embodiments, streams of materials or mineral ores may be transported using one or more conveyor belts, vibratory feeders, mining shovels, scoop-trams, or other mechanisms. Mineral ore streams may be diverted by means of alternative disposition of the mechanism itself (e.g., the shovel) or by means of diverters on the mechanism. In some embodiments, sensors are used to determine the grade of a mineral ore stream and decide which way to divert it. For instance, the content of an individual ore-bearing rock being transported on a conveyor belt may be determined by a high-frequency electromagnetic sensor to be below or above an arbitrary cutoff value and diverted, accordingly, to the waste pile or the process queue, respectively. Sensor types include electromagnetic, laser breakdown, X-ray fluorescence, gamma and other sensor types used in the sorting of materials or mineral ores. In some embodiments, one or more high frequency electromagnetic spectrometers ("HFEMS") may be used. These mechanisms are shown in other figures and described herein.

In block 110, mineral ores are collected by means of a mining shovel or scoop-tram or other arrangement known in the art. The mineral ores may be collected from a stockpile or bench or other arrangement known in the art.

In block 120, the mineral ores are classified into streams based on grade. The classification may be done for various sample sizes. Grade of the value-bearing mineral ores may be determined by electromagnetic sensing, for example, which is described in further detail below. In some embodiments the streams include lower-grade, higher-grade, and waste streams. The higher-grade streams contain ore with a higher grade than the material in the lower-grade stream and the lower grade stream has a higher grade than the material in the waste stream. The classification may be determined by pre-set values, e.g., based on a selected threshold such as a percentage of an element within the mineral ore. Any mineral ore with a content value higher than a pre-set value will be classified as higher-grade. The streams may be diverted by means of diversion using the mining shovel bucket or scoop-tram bucket itself, or by belt conveyor in conjunction with a diverter gate or mechanical flaps or compressed air ejector mechanisms. In some embodiments, the mineral ores are classified using sensors on a mining shovel, scoop-tram, or belt-conveyor.

In block 130, after the classifying, the lower grade and higher grade streams are prepared for sorting. In some embodiments, preparing for sorting includes coarse crushing and size classification. In some embodiments, the size classification may be wet size classification. In some embodiments, the preparation further includes dividing the higher-grade and the lower-grade streams into sub-streams based on particle size for improved sorting performance.

In block 140, the larger particle size stream of the higher-grade stream is sorted into groups based on grade. The groups may include a higher-grade group and a lower-grade group. The values of the grades used to determine the groupings may include pre-set values.

In block 150, the lower-grade subgroup of the larger-particle size group of the higher-grade stream is combined with the larger particle size subgroup of the lower-grade group.

In block 160, the combined group of block 150 is sorted into subgroups including a higher-grade subgroup and a lower-grade subgroup. The groups may be determined by preset grade values, or the groups may be based on values determined during the sorting process.

Figure 2:
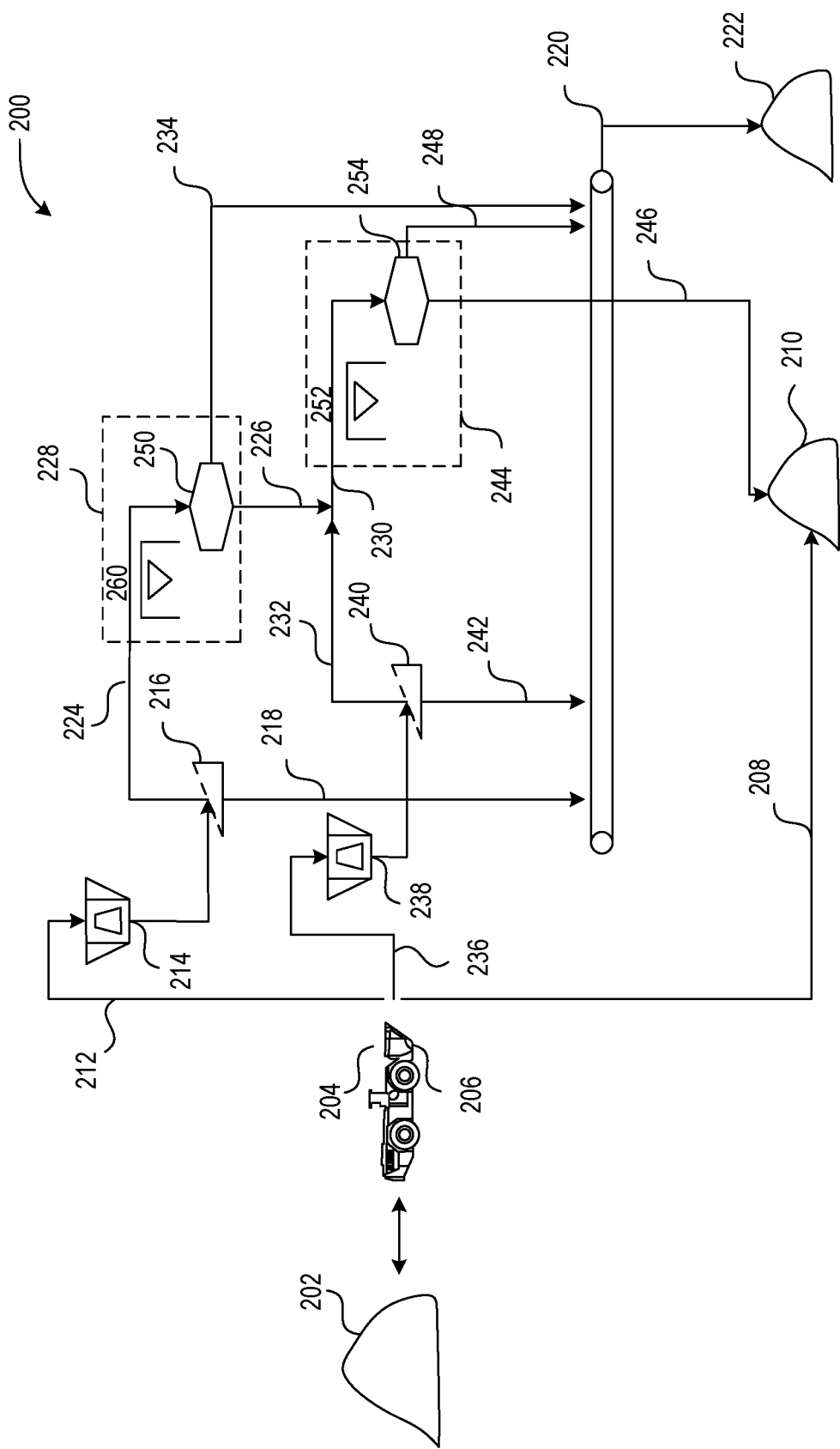
FIG. 2 illustrates a system for extracting materials.

System for Extracting Materials:

FIG. 2 illustrates a system 200 for extracting materials. In accordance with embodiments of the invention, a system for extracting materials may include a primary sensing and diversion mechanism, feed preparation system, higher-grade sorter systems, lower-grade sorter systems, waste handling system, and product handling system. System 200, includes ore 202, mining shovel, scoop-tram or similar device 204, sensor or device for sensing 206, waste stream 208, waste pile 210, higher-grade stream 212, coarse crusher 214, and screen 216. The system also includes smaller particle size substream 218 of the higher-grade stream 212, final product stream 220, final product pile 222, and larger particle size substream 224 of the higher-grade stream 212. Further, the system includes lower-grade substream 226 of the larger particle size substream 224 of the higher-grade stream 212, higher-grade sorter system 228, combined stream 230, higher-grade substream 234 of the larger particle size substream 224 of the higher-grade stream 212, lower-grade stream 236, lower-grade coarse crusher 238, lower grade sizing screen 240, smaller particle size substream 242 of the lower-grade stream 240, larger particle size substream 232 of the lower-grade stream 236, lower-grade sorter system 244, lower-grade substream 246 of the combined stream 230, higher-grade substream 248 of the combined stream 230, higher-grade stream sensor 260, higher-grade stream sorter 250, lower-grade stream sensor 252, and lower grade stream sorter 254. Various embodiments include some or all of these components.

In one embodiment of system 200 in operation, ore 202 from a bench in the mine or from a stockpile is collected by mining shovel or scoop-tram 204. Variations of the particular mining shovel or scoop tram provide equivalent methods of mounting the invention, and as such, the invention is not limited to one specific arrangement of mining shovel. The bucket of the mining shovel or scoop-tram 204 may be fitted with a spectrometer or other sensor type 206 for the sensing of the ore composition in the bucket. In a different embodiment, a bucket may scoop the ore onto a conveyor belt equipped with sensors to perform spectrometry as the ore moves along the belt. Variations of the particular spectrometer or other sensor type provide equivalent methods of mounting the invention, and as such, the invention is not limited to one specific arrangement of spectrometer or other sensor type.

The composition of the mineral contained in the bucket as measured by the spectrometer or other sensor type 206 is compared to a pre-set value and a decision is made by the operator or made automatically by a computer or other signal or data processing device. The system diverts or sends mineral content below a certain pre-set value to a waste stream 208. As shown, waste stream 208 is diverted to a waste pile 210. In contrast, the system passes minerals of a content above a certain pre-set value to a higher-grade stream 212. As shown, the higher-grade stream 212 is passed to a feed preparation system comprising a higher-grade stream coarse crusher 214 and higher-grade sizing screen 216. Variations of the particular crusher and sizing screen provide equivalent methods, and as such, the invention is not limited to one specific arrangement of crusher or sizing screen.

The system passes material previously determined to be below a certain particle size from the higher-grade stream sizing screen 216 to smaller particle size substream 218. Smaller particle size substream 218 of the higher-grade stream 212 is passed directly to the final product stream 220, and delivered to the final product pile 222. Material above a certain particle size is passed to the larger particle size substream 224 of the higher-grade stream 212. The larger particle size substream 224 is passed to the higher-grade sorter system 228. The higher-grade sorter system 228 uses sensor 260 and higher-grade stream sorter 250 to sort the larger particle size substream 224 into a lower-grade substream 226 and a higher-grade substream 234 based on grade, where the lower-grade substream has a lower grade than the higher grade substream. The lower-grade substream 226 is combined with the larger particle size substream 232 of the lower-grade stream 236, and delivered to the combined stream 230. Higher-grade substream 234 is passed to the final product stream 220, or the minerals are directly passed to the final product pile 222. Variations of the particular mineral sorter provide equivalent methods, and as such, the invention is not limited to one specific arrangement of mineral sorter.

Returning now to the scoop tram or mining shovel 204, low-grade material between the lower pre-set value and the upper pre-set value is passed to lower-grade stream 236. Lower-grade stream 236 is passed to the feed preparation system comprising coarse crusher 238 and sizing screen 240. Variations of the particular crusher and sizing screen provide equivalent methods, and as such, the invention is not limited to one specific arrangement of crusher or sizing screen. Material below a certain particle size previously determined is passed to a smaller particle size substream 242. The smaller particle size substream 242 is passed directly to the final product stream 220. Material above a certain particle size is passed to a larger particle size substream 232. The larger particle size substream 232 is combined with the larger particle size substream 226 to form combined stream 230. The combined stream 230 is passed to the lower-grade mineral sorter system 244. The lower-grade mineral sorter system 244 sorts the minerals into a lower-grade substream 246 and a higher grade substream 248 using sensor 252 and lower-grade stream sorter 254. The lower grade substream 246 is passed to the waste pile 210. The higher-grade substream 248 is passed to the final product stream 220. Variations of the particular mineral sorter provide equivalent methods, and as such, the invention is not limited to one specific arrangement of mineral sorter.

The high-grade mineral sorter system 228 comprises a higher grade stream sensor 260 and a higher grade stream sorter 250. The composition of the larger particle size substream 224 is measured by the higher grade stream sensor 260. The higher grade stream sensor 260 passes information relating to the composition of incoming feed material to the higher grade stream sorter 250 in order to set an appropriate value for the lower-grade substream 226 cutoff. The contents of the lower grade substream are rejected and combined with the large particle size substream 232 of the lower-grade substream 236 to form the combined stream 230. The contents of the higher-grade substream 234 are passed to the final product stream 220.

The low-grade mineral sorter system 244 comprises a lower grade stream sensor 252 and a lower-grade stream sorter 254. The combination of the larger particle size substream 232 and the lower grade stream 226 of the larger particle substream 224 of the higher grade stream 212 passed to the lower-grade stream sorter 254 is measured by the lower-grade stream sensor 252. The lower grade stream sensor 252 passes information relating to the composition of the feed material to the lower grade stream sorter 254 in order to set an appropriate value for the waste rejection cutoff. Valuable material above the cutoff is accepted and passed to the final product stream 220 via the higher grade substream 248. Material rejected by the low-grade sorter 254 enters lower-grade substream 246, where it is passed to the waste pile 210.

The various streams shown and described in FIG. 2 are examples. Other streams are contemplated, as well as the combination of certain streams. For example, the streams that feed into the final product stream 220 could bypass the final product stream 220 and go straight to the final product 222.

Figure 3:
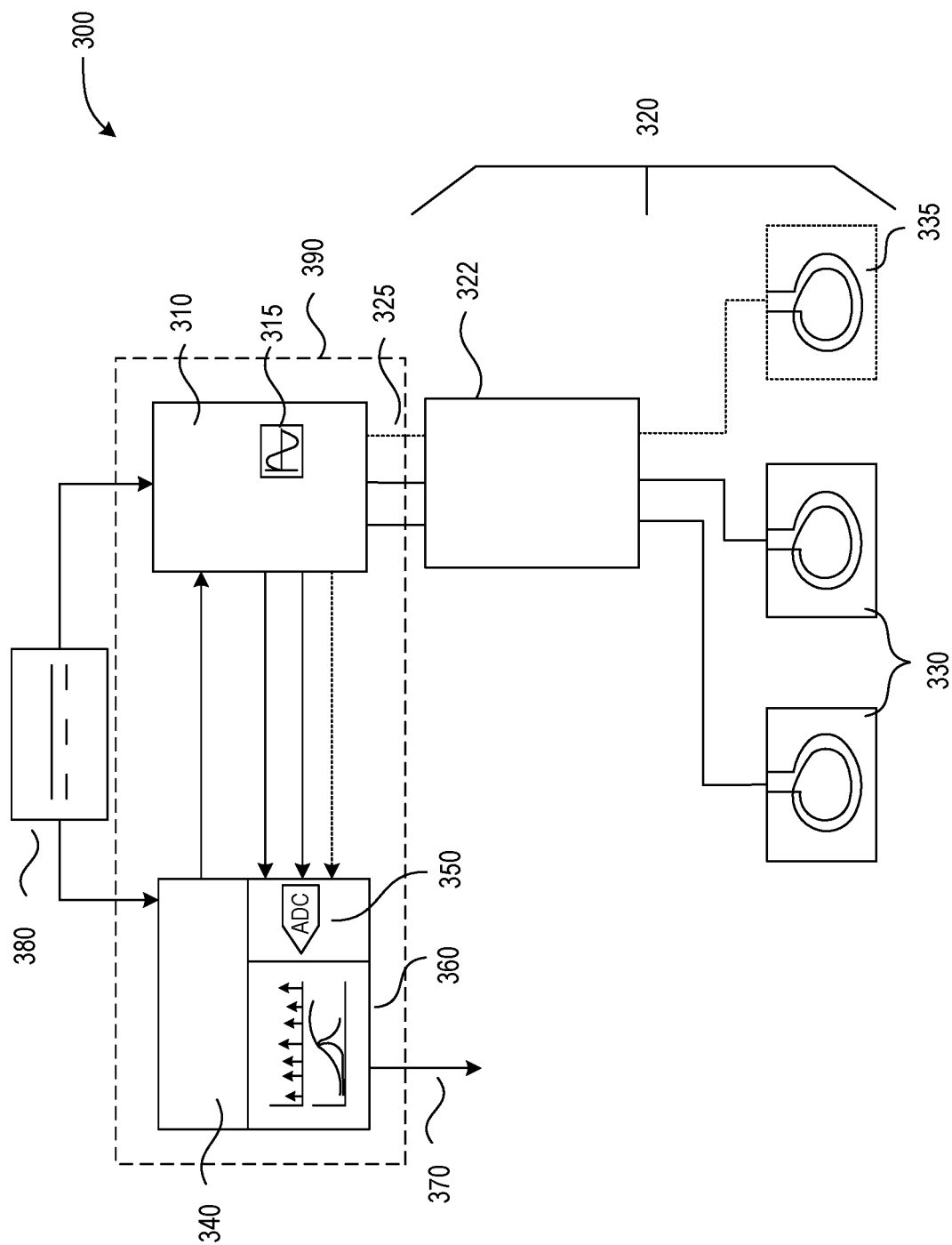
FIG. 3 is a block diagram of a sensor system that may be used in methods and systems for extracting materials.

Sensor System Details:

FIG. 3 is a block diagram of a sensor system that may be used in methods and systems for extracting materials. The sensor system 300 may be used in the high grade and low-grade sorter systems, for example, or the sensor system may be used in connection with other mining equipment such as a mining shovel or a conveyor belt system.

Referring to the components of sensor system 300, in the signal conditioning electronics 310, the output of a waveform generator 315, such as a user-selected multi-frequency arbitrary waveform, is conditioned and applied to a balanced bridge network 320, comprising active sensors (coils or an array of coils) 330, a reference sensor 335 and bridge circuitry 322. The output of the arbitrary waveform generator 315 is controlled by a data processor, such as an industrially hardened computer 340, although any computer, microcontroller, data processor or logic may be employed. The bridge network output signal 325, which is the output from the bridge network 320 is sent through additional signal conditioning electronics 310 and is digitized by analog to digital converter 350. The captured data is processed and analyzed by a computer software program 360, running on an industrially hardened computer 340. The computer software 360 converts the bridge network output signal 325 into response data, and generates a control and data output 370 based on the value of the response data. A regulated DC power supply 380 provides power to the integrated circuits in the signal conditioning electronics 310, and the industrially hardened computer 340. The dashed lines indicate one arrangement of the components; an industrially hardened computer 340, with analog to digital converter 350, a signal generation and signal conditioning circuit including a bridge network 320 of one or more active sensors 330 and a reference sensor 335; data output hardware 370, and a DC power supply 380. The industrially hardened computer analog to digital converter and data output are housed in a protective enclosure 390. Bridge network sensors and electronics 320 are housed in a sensor chassis.

The signal conditioning electronics 310 may be designed into fully functional modular units comprising a microcontroller, a waveform generator 315, which may be an arbitrary waveform generator, and a power amplifier; the bridge network 320 comprises bridge electronics with filter and gain stages integrated with the sensor array. Multiple modules can be combined to increase the number of sensor arrays in a system. The industrially hardened computer controls operation of the signal conditioning electronics circuit and generates output data based on the signal of each individual sensor. The output of waveform generator 315 may be selected and/or tuned based on testing or empirical analysis of minerals to be detected. Waveform types and frequencies, and all amplifier gain stages are controlled by the microcontroller and are user-selectable through the industrial hardened computer. The arbitrary waveform generator 315 is capable of producing user-selectable arbitrary waveforms, including single frequency signals of specifiable shape, amplitude and frequency, composite signals of multiple frequencies, frequency sweep signals with specifiable range, and DC signals. Variable gain amplifiers before and after the bridge network 320 allow for control of signal levels. The generated waveform is then conditioned to drive the bridge network, and the bridge output is then conditioned to drive the analog to digital converter.

The balanced bridge network 320 comprises an array of multiple sensing coils 330 used to examine samples, and in at least one embodiment, a reference sensor 335 used as a reference to the sensing coils. The reference sensor 335 may include coils and is used to balance the bridge network. In some embodiments, there is more than one reference sensor. For example, there may be one reference sensor per array of sensing coils. The reference sensor 335 is subject to the same electrodynamic environment as the sensing coils 330, but is kept physically isolated from the mineral stream to be examined. In the presence of mineral samples of metallic content, the impedance of a sensing coil 330 no longer matches that of the reference sensor 335. This impedance change unbalances the bridge network, producing a voltage signal of magnitude and phase related to the change in resistive and reactive components of the sensing coil impedance. In some embodiments, multiple arrays of coils can be used, in which each array has one or more sensor coils and at least one reference sensor.

The unbalanced signals from each sensing coil 330, along with a reference of the excitation signal from the reference sensor 335 are sent back through the signal conditioning electronics 310, where they are conditioned for output to the analog to digital converter 350. The analog to digital converter 350 is capable of real-time, or substantially real time, data streaming into the industrially hardened computer and is used to digitize the sensor output signals for analysis by the software program 360. Depending on the type of sample examined, and the nature of the input signal, the sensors may produce an unbalanced signal with a change in magnitude only or a combination of magnitude and phase changes for each frequency of excitation. Signals captured thus from the bridge network undergo Fast Fourier Transform operations to extract and analyze spectral information from the sensors. The change in the individual impedance of each active sensing coil 330 is then calculated. From this impedance value the quantity of conductive and magnetic material in the media or sample present over each sensor is calculated. Data relating to the value of conductive and magnetic material in the samples present over each sensor is then transmitted to external devices by the industrially hardened computer. Depending on the application, this data can be individual sensor response values, or instructions to an external device based on comparison of individual sensor response values to a user-defined setpoint. In some embodiments, only differences in impedance between individual active sensors in the array and the reference sensor are of use in the system. Although only one reference sensor is shown in FIG. 3, numerous reference sensors may be used.

The power supply 380 is a common component with internal operations, with the purpose of providing a DC voltage as required by integrated circuits in the signal conditioning electronics 310, and the industrially hardened computer 340.

Overall, while one form of sensor, its arrangement and circuitry are described herein, many others are possible. Various sensors may be used in connection with extracting materials, including sensors described in CIPO 2629408, which is hereby incorporated by reference for all purposes in its entirety.

Sensor System Operations:

The following is a description of one embodiment of a sensor system. Other types of sensors and sensor systems are contemplated. For example, sensor types may include, but are not limited to electromagnetic, laser breakdown, X-ray fluorescence, and gamma. Alternative embodiments using HFEMS is contemplated where the analog to digital conversion takes place not in a general purpose computer but at or near the bridge network.

Referring to the embodiment shown in FIG. 3, in operation, the sensing coils 330 each produce a static field in the surrounding environment when excited by a DC current, and a dynamic field in the surrounding environment when excited by an alternating current, related in frequency and strength to the signal from the signal conditioning electronics 310. Samples are placed on or passed over the active sensors 330. The sensing coil field completely penetrates the sample, immersing conductive, magnetic and paramagnetic media contained in the sample within the sensing coil field. Electric currents are thus induced in the conductive, magnetic or paramagnetic material present in the samples passing through the sensing coil field 330. These currents generate magnetic fields with strength in respect to the amount of conductive material in the sample, which in turn generate counter-currents in the coil, changing the impedance of the coil-conductor system as seen across the coil 330. This change in impedance unbalances the bridge network 320 with respect to the reference sensor 335, and changes the bridge network output signal 325. For the sensing of magnetic or paramagnetic material, the sensors are excited by a direct current (DC). Magnetic material passing through or present within the sensor field alters the impedance of the coil 330, altering the current passing through the coil. This change in impedance in the sensing coil 330 changes the bridge network output signal 325 with respect to the reference sensor 335. The reference sensor 335 is not exposed to conductive or magnetic material. Output signals from the bridge network are captured by the analog to digital converter 350. Signals thus captured undergo Fast Fourier Transform in the analog to digital converter 350 to extract and analyze spectral information. The magnitude and phase components of the change in the individual impedance of each sensing coil 330 are calculated for the AC case. The change in the individual impedance of each sensing coil 330 is also calculated for the DC case.

For initial calibration, the actual content of conductive and magnetic material in a sample is measured by chemical assay. The actual content of conductive and magnetic material as measured by chemical assay is then correlated to the spectral output of the sensors. The actual content of similar material passing over the sensors can then be determined directly by the system. The instantaneous and time-averaged measure of metallic content as determined by each coil 330 is communicated to other devices via the data output hardware 370. The present invention is not limited to the operations described with respect to figure three.

Figure 4:
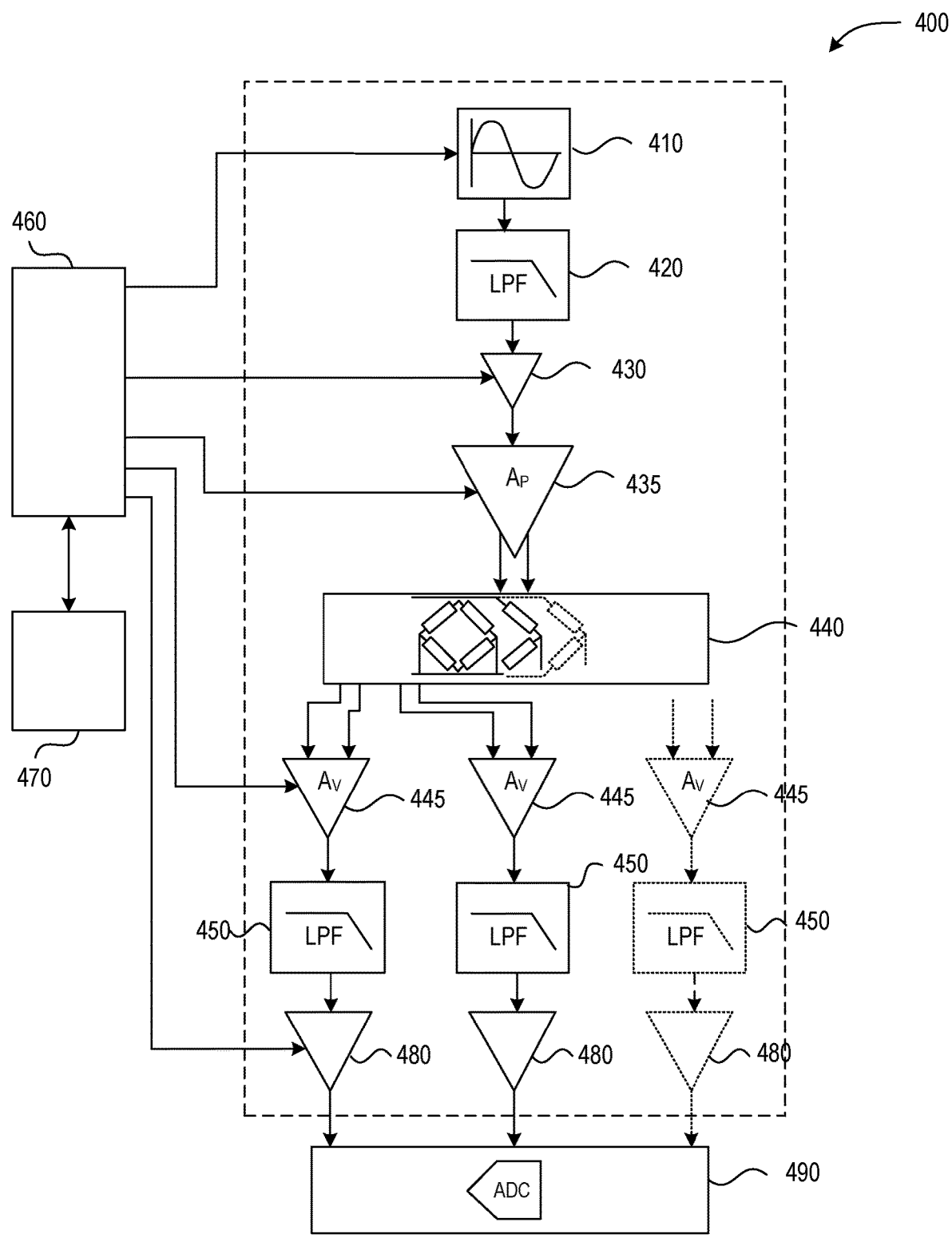
FIG. 4 is a signal flow diagram illustrating circuitry of a sensor that may be used in the methods and systems for extracting materials.

Sensor Circuitry:

FIG. 4 is a signal flow diagram illustrating circuitry 400 of a sensor that may be used in the methods and systems for extracting materials and mineral ores. Referring now to the individual system components in more detail, there is shown a signal flow diagram of the signal conditioning electronics and bridge circuitry. The signal conditioning electronics includes a signal source such as an arbitrary waveform generator 410, an input filter stage 420, a preamplifier stage 430, a power amplifier with differential output 435; the balanced bridge network 440 comprises the active coil array 330 and matched reference sensors 335, in a bridge arrangement 440 with amplification by amplifiers 445, and filtering stages by filters 450 on each of the output channels. Control of the waveform generator 410, and amplifiers 430, 435, 445 is performed by the microcontroller 460 using user-defined values sent from an industrially hardened computer 470. The frequencies generated by the signal generator, such as the arbitrary waveform generator 410, are decided in advance based on initial calibration described above. For example, the ore may be tested in a lab or field prior to beginning the sorting process to determine responses. The signal generator may be programmed by the user to generate the particular frequencies to which the ore of interest has shown the greatest response. Pre-determining the frequencies to be applied and the expected responses enables the sorting process to be selective, allowing the system to analyze a great amount of material in a short amount of time.

The microcontroller 460 instructs the waveform generator 410, (which may be an arbitrary waveform generator) and the resulting output forms the basis of the sensor input signal. The input filter 420 is a low-pass filter with a cutoff frequency greater than the highest frequency component of the input signal. The filter is used to smooth the generated signal and remove spectral images produced by the waveform generator 410. The preamplifier stage 430 sets the signal level applied to the bridge network 440. The preamplifier gain is determined by a value sent from the industrially hardened computer 470 to the microcontroller 460. The differential outputs of the power amplifier 435 are used as the driving current to excite the bridge network 440, providing balanced positive and negative signals. The power amplifier 435 can be shut down by the microcontroller 460 based on a control signal from the industrially hardened computer 470.

The implemented bridge network 440 is a modified Wheatstone bridge used to measure impedance differences between bridge components in the form of a voltage signal. The bridge is modified to allow for an array of matching sensors balanced by a single reference sensor. Variations of the Wheatstone bridge, and other bridge networks, provide equivalent methods of detecting impedance differences, and as such, the invention is not limited to one specific bridge network arrangement.

In an ideal rest state with sample present, the bridge network 440 is perfectly balanced, and no voltage is seen across the bridge. Error tolerances in real components create an inherent imbalance in the bridge network 440, producing an unbalanced voltage signal even in the rest state. The ambient environment also affects the bridge balance, such that the rest state unbalanced voltage of a given sensor system may differ between operating locations. The industrially hardened computer 470 calibrates the system by interpreting this rest state signal as a baseline response against which successive readings are measured.

Since the bridge network 440 can be driven by a direct current or alternating current signal, the unbalanced voltage signal is measurable in magnitude alone, or in magnitude and phase with respect to the input signal. Output signals are a reference of the input signal and the unbalanced signal from the bridge network 440. The output signals pass through differential amplifiers 445 for common mode rejection of any induced circuit noise. Low pass anti-aliasing filters 450 remove high frequency noise from the signals to prevent analog-to-digital conversion errors. Variable gain buffer stages 480 controlled via the microcontroller 460 condition the signals for driving the analog to digital converter 490. The analog to digital converter captures the reference and unbalanced signals from each of the sensors in the bridge network, and performs Fast Fourier Transform operations to extract and analyze spectral information from these signals. From this information the quantity of conductive and magnetic material in the sample is calculated. The response of the system to samples of known conductive or magnetic content has been determined as previously described in 0044. The actual content of metallic material as measured by chemical assay is then correlated to the spectral output of the sensors. The actual content of similar material passing over the sensors can then be determined directly by the system. Thus, the measurements may be converted to ore grade values by using the correlations determined earlier by assay/testing. Additional improvements in processing allow for the necessary calculations to be performed more quickly than in prior art systems. Additional improvements in processing allow for the necessary calculations to be performed more accurately than in prior art systems. Due to the selective nature of the sorting and processing speed, a great amount of material can be analyzed in a short amount of time to thereby grade ore in a more commercially valuable manner. Other equivalent arrangements are easily conceivable, and the invention is not limited to the arrangement described above.

Figure 5:
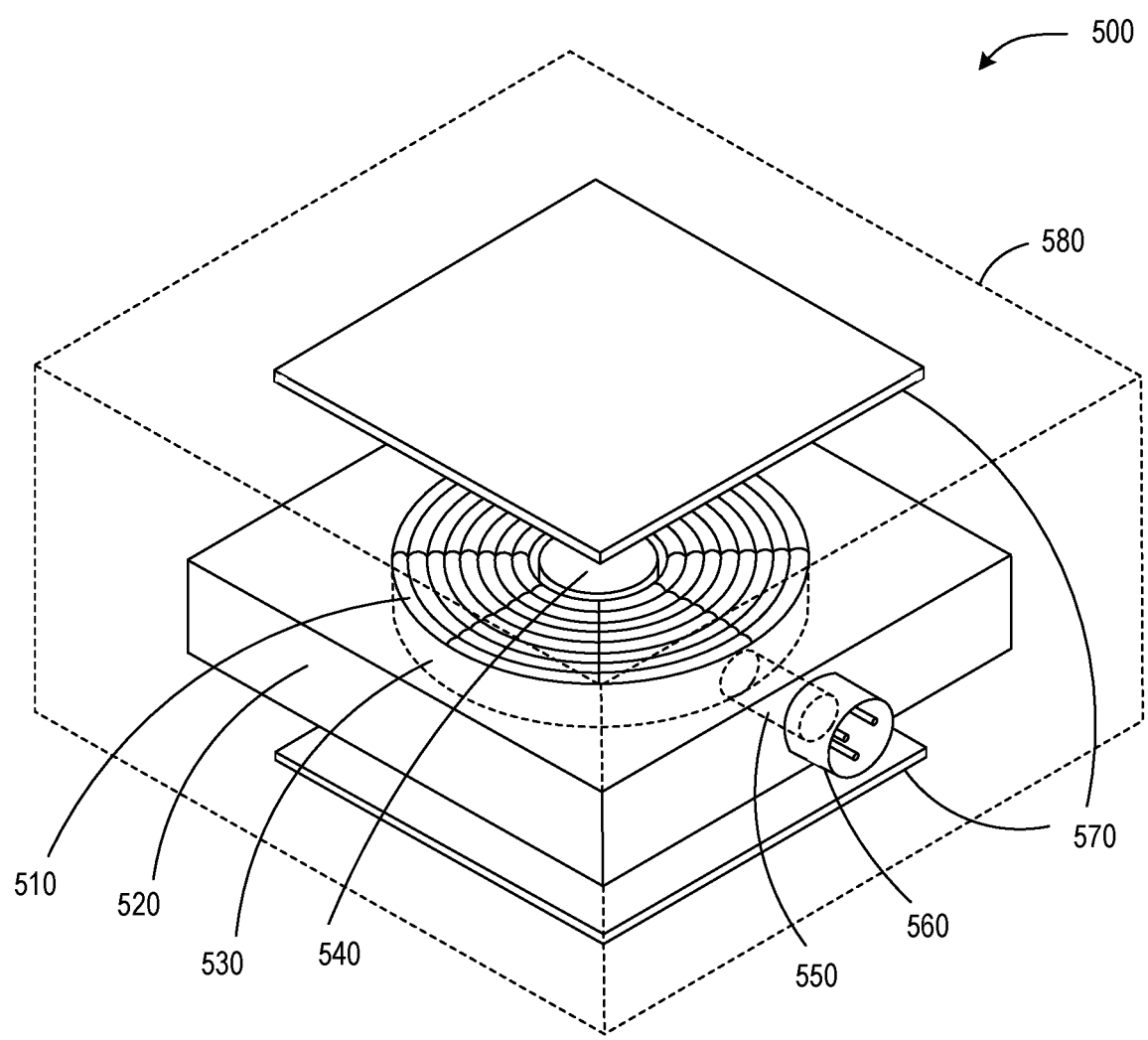
FIG. 5 illustrates a coil and coil housing that may be used in methods and systems for extracting materials.

Coil Arrangements for an HFEMS Sensor:

FIG. 5 illustrates a coil and coil housing that may be used in methods and systems for extracting materials. The present invention is not limited to the arrangement shown in FIG. 5. In some embodiments, the coil and coil housing are components of the electromagnetic sensor system discussed above. The coil 510 rests in a polycarbonate base 520 with a circular groove 530 routed around a center boss 540. The coil 510 is produced by feeding one end of a wire though a cable hole 550 in the side of the base 520 and wound in alternating layers from the outer edge of the groove 530 inward to the boss 540, then outward from the boss 540 to the outer edge of the groove 530. The free ends of the coil 510 exit the base through the cable hole 550, and terminate at a connector 560 mounted on the base. Electrostatic shields 570 are placed above and below the coil 510 to bound the field extents and limit electromagnetic interference. The entire sensor coil and base is enclosed in a polycarbonate housing 580. In the shovel-bucket embodiment, such as in FIG. 8, the coils may be housed inside cast blocks of ultra-high molecular-weight polyethylene for impact and wear resistance when exposed to hard and abrasive mineral streams. While impact and wear resistant, the coils are designed to match the impact and wear resistance of the surrounding bucket environment and enjoy similar replacement intervals to surrounding materials. Further, the specific arrangement of the sensors in the bucket within and among the wear materials in the bucket allows for protection of and therefore use of sensitive coil arrangements in the high impact and wear environment of the shovel bucket. Further, the specific size and orientation of the sensors is unique to the particular bucket, and determined by the desired coverage of the shovel bucket volume by the combined fields of the coils in the array. Coils are an order of magnitude more compact than in prior art systems, and the implementation of this coil type with arbitrary waveform excitation in the induction-balance arrangement is a departure from prior art systems.

Figure 6:
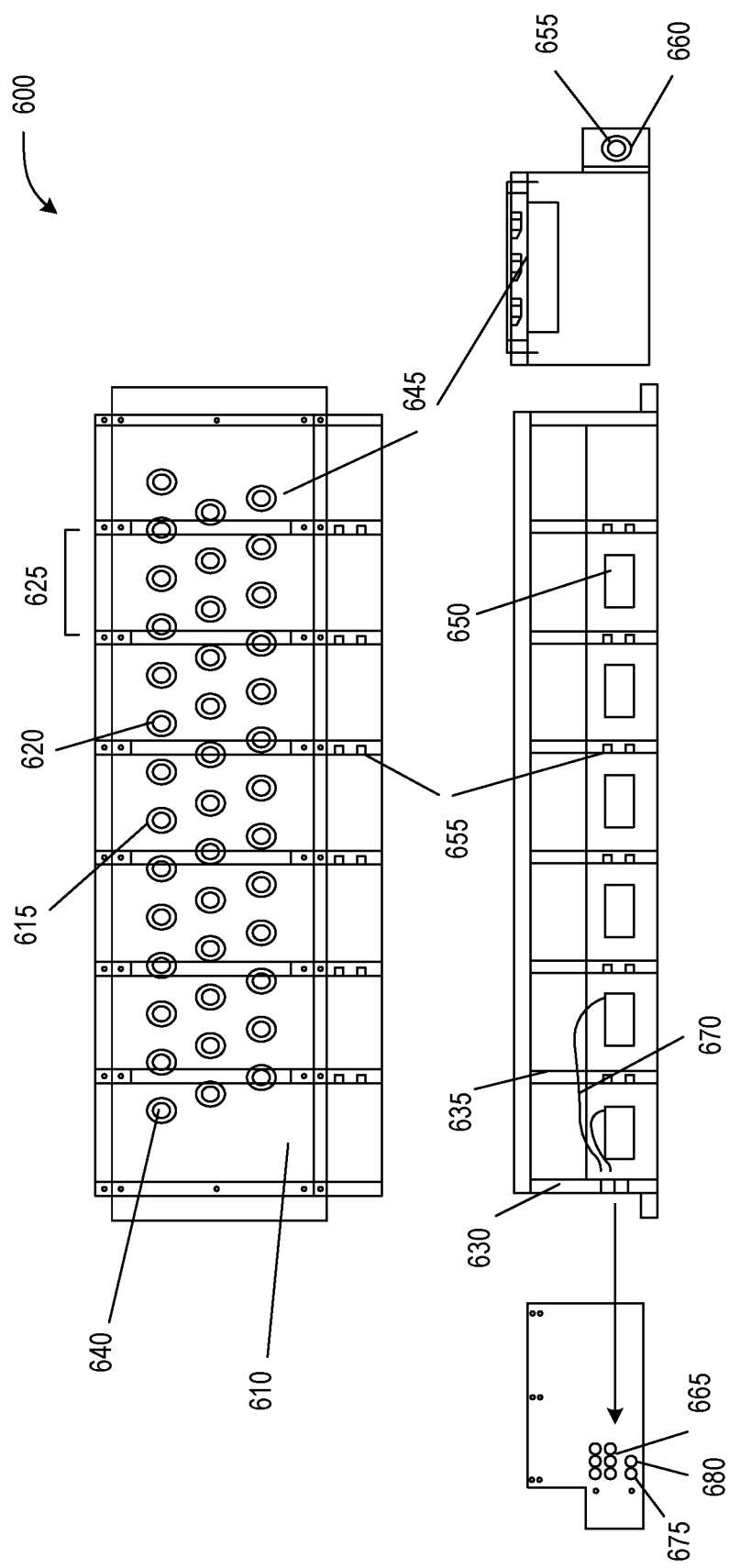
FIG. 6 illustrates a plan and section view of coil array and coil array housing that may be used in methods and systems for extracting materials.

FIG. 6 illustrates a plan and section view of coil array and coil array housing that may be used in methods and systems for extracting materials using HFEMS in the sorting embodiment. Each coil array includes multiple coils per a single bridge. In some embodiments, the arrangement of coil array and coil housing shown 600 is used in an electromagnetic sensor system, such as the electromagnetic sensor system described above. FIG. 6 includes a plan and section view 600 of the coil arrays 330 and bridge electronics 440 in the coil array housing.

Multiple coils rest in a top plate 610 with circular grooves 615 routed around a center boss 620 to house the coil conductors. The coils are arranged in arrays 625 Multiple arrays 625 are possible in any embodiment, in this case six. The top plate is mounted on a chassis 630 with interior ribs 635 for coil support and electrostatic shielding. The free ends of the coils 640 exit the base through the cable hole 645, and terminate at the localized bridge board 650 mounted in the chassis. One reference sensor 655 is required per localized bridge 650, and is mounted vertically in the toe of the interior rib 635. The free end of the reference sensor exits through the base hole 660 and terminates at the localized bridge board 650 mounted in the chassis. Amplified signals from all the coils 640 in an array 625 connected to the localized bridge board 650 are transmitted to the terminal block 665 via 22-conductor bundled shielded conductor cable 670. Similarly, signals from coil arrays 625 connected to other bridge boards 650 are transmitted to the terminal block 665 via 22-conductor bundled shielded conductor cables 670. Thus, cables may be used to separate the coils from the bridge. The cables may be armored and shielded signal cables, allowing placement of the sensors in harsh environments. In one embodiment, up to 6 localized bridge boards 650 are contained in the coil array housing 630, allowing for 6 sensor arrays 625 to be used. Source signals from a signal generator such as signal generator 410 are delivered to each board in parallel via signal cables 675. Power is delivered to each localized bridge board in parallel via a power cable 680. Other equivalent arrangements are easily conceivable, and the present invention is not limited to the described arrangement. For instance, there may be any number of sensor coils in each local arrangement. They may be encased in a variety of materials. The wires may vary in conductance, and in their materials. The arrangement of previously described compact coils in an array and in the induction-balance configuration, is a significant improvement on prior art embodiments.

Figure 12:
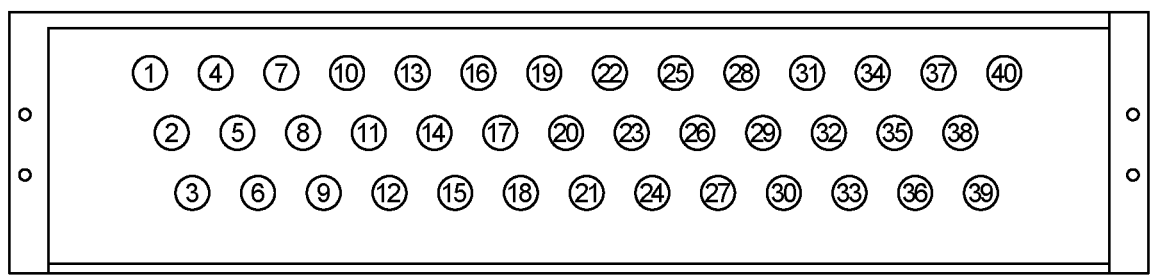
FIG. 12 illustrates a coil array that may be used in methods and systems for extracting materials.

The sensor can be arranged in many different ways, and the sensors may be scaled to any relevant size appropriate for the duty. For example, the sensors may be scaled to perform electromagnetic spectroscopy depending on the particular sample size. For example, the sensors for approximately 1 millimeter samples may be about 1 millimeter in diameter, and the sensors for approximately 12.5 millimeters may be approximately 12.5 millimeters. FIG. 12 illustrates another view of a suitable coil array arrangement.

The HFEMS sensors described are both inexpensive and durable. Due to the harsh environment the sensors are exposed to, durability is a desired feature of sensors. Although durable, the HFEMS sensors will require replacement at some point, so naturally, economics are a consideration as well. In a preferred embodiment, the lifetime of the sensor corresponds with the maintenance schedule of the device with which the sensor is interconnected. In the systems described herein, the sensors collect information, but do little or no processing of the information collected. The processing and analytics of the information takes place away from the sensors, and the related processing equipment is not subjected to the harsh environment to which the sensor is subjected. Thus the sensors may be designed to be "consumable goods". Thus, a sensor may be formed on, or within grooves of, first, replaceable substrate, such as a metal plate, with a second, protective surface or ablative plate formed over the first substrate. Any manner of mechanical fasteners may be used to secure the sensor(s) to a bucket, such as simply a threaded bolt with corresponding nut.

Figure 7:
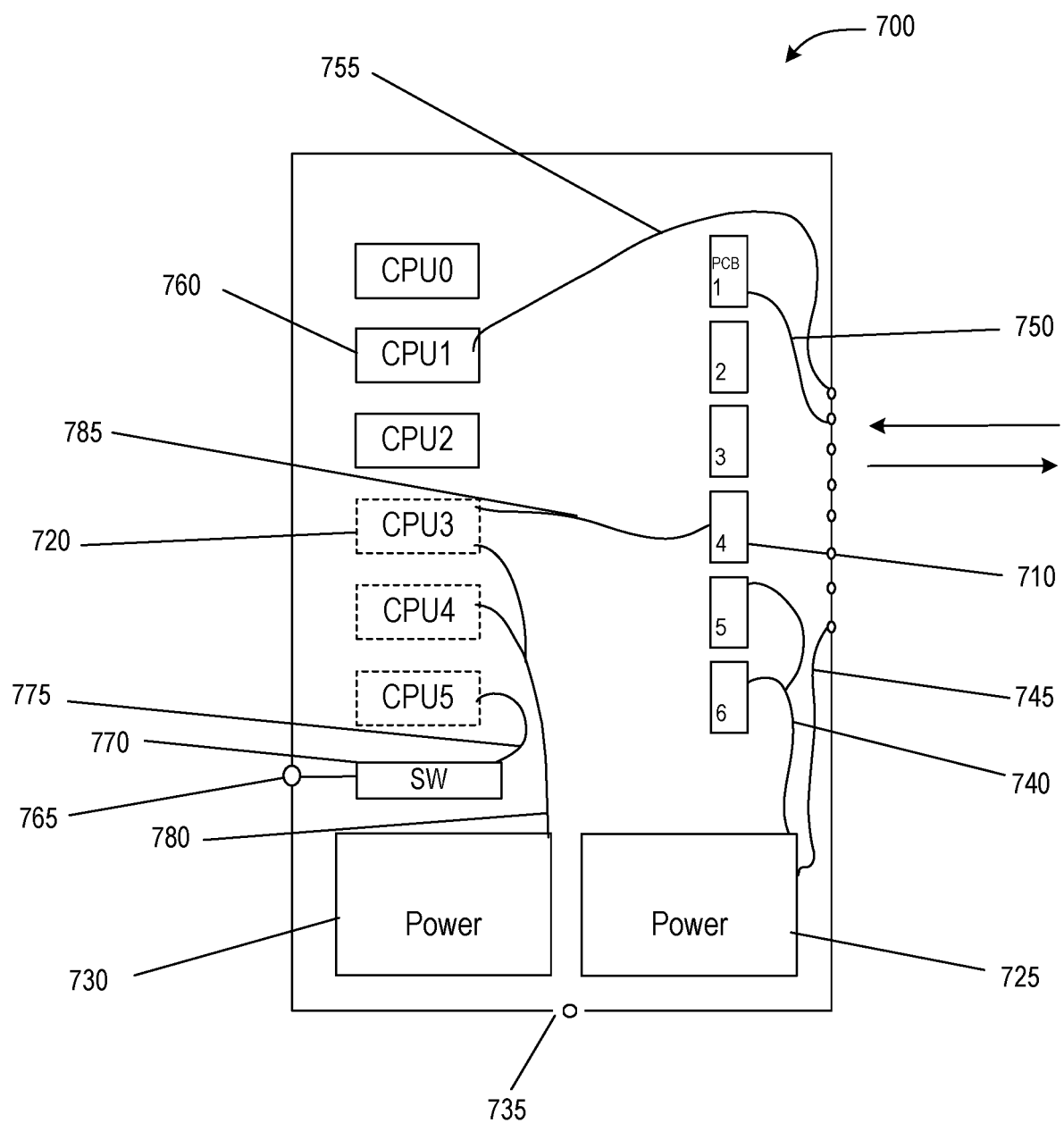
FIG. 7 is a diagram of control electronics and digital signal processing system enclosure that may be used in methods and systems for extracting materials.

Control Electronics and Digital Signal Processing System:

FIG. 7 is a diagram of the control electronics and digital signal processing system enclosure that may be used in methods and systems for extracting materials. In some embodiments, the control electronics and digital signal processing system is used in an electromagnetic sensing system, such as the system discussed above. Referring now to the individual system components in more detail, in FIG. 7 there is shown a view of the control enclosure 700, containing the signal generation electronics 710 and the industrially hardened computer 720. 110V or 220V power as the case may be is delivered to each of the power supplies 725, 730 in the control enclosure via main cable 735. Power at 10V from the sensor power supply 725 is delivered to the signal generator boards in the signal generator electronics 710 in parallel via a DC power cable 740. Power at 10V from the sensor power supply 725 is also delivered to the localized bridge boards 650 via 22-conductor bundled shielded conductor cable 745. Source signals from the signal generators 440 are delivered in parallel to the localized bridge boards 650 in the sensor block via a 22-conductor bundled shielded conductor cable 750. Power at 10V from the digital computing power supply 730 is delivered to the industrially hardened computer 720 in parallel via DC power cable 780. The signal generator function of the signal generators 440 is controlled by the user via the industrially hardened computer 720.

Active signals from the localized bridge boards 650 are delivered to the analog to digital converter 760 inside the industrially hardened computer 720 via 22-conductor bundled shielded conductor cable 755. Active signals from each localized bridge board 650 transmitted via cable 785 are processed by Fast Fourier Transform by the analog to digital converter 760 and transmitted to the industrially hardened computer 720. The resulting metallic content of particles within the sensor field is calculated by the computer software 765. Metallic content thus calculated for particles within the field of sensors is compared to a user-defined reference value stored in the software in order to make a sort decision. Metallic content below the reference value of sensor n results in a sort signal that is different from the sort signal generated for metallic content above the reference value. The sort signal generated for sensor n is transmitted from the industrially hardened computer 720 to the multiport switch 770 via cable 775. In some embodiments, an open platform digital communications protocol (UDP or industrial TCP/IP, for instance) is used for data transmission and sensor control, which may be less costly to implement and maintain. In other embodiments, proprietary industrial protocols such as ModBus or Profibus may be used. Other equivalent arrangements are easily conceivable, and the present invention is not limited to the described arrangement.

Sensor-Based Sorting Apparatuses and Systems:

FIGS. 8-11 illustrate various apparatuses and systems in which sensors may be used. As discussed above, various types of sensors may be used, such as the HFEMS sensors. In various applications, such as the below examples, there need not be any electromagnetic difference between the HFEMS coils. However, the protective substrate, cover or liner materials may be different based on the particular application, with a view to synchronizing the replacement of these consumable materials with the maintenance schedule of the device to which they are connected. This synchronization minimizes costs as well as providing other benefits.

Figure 8:
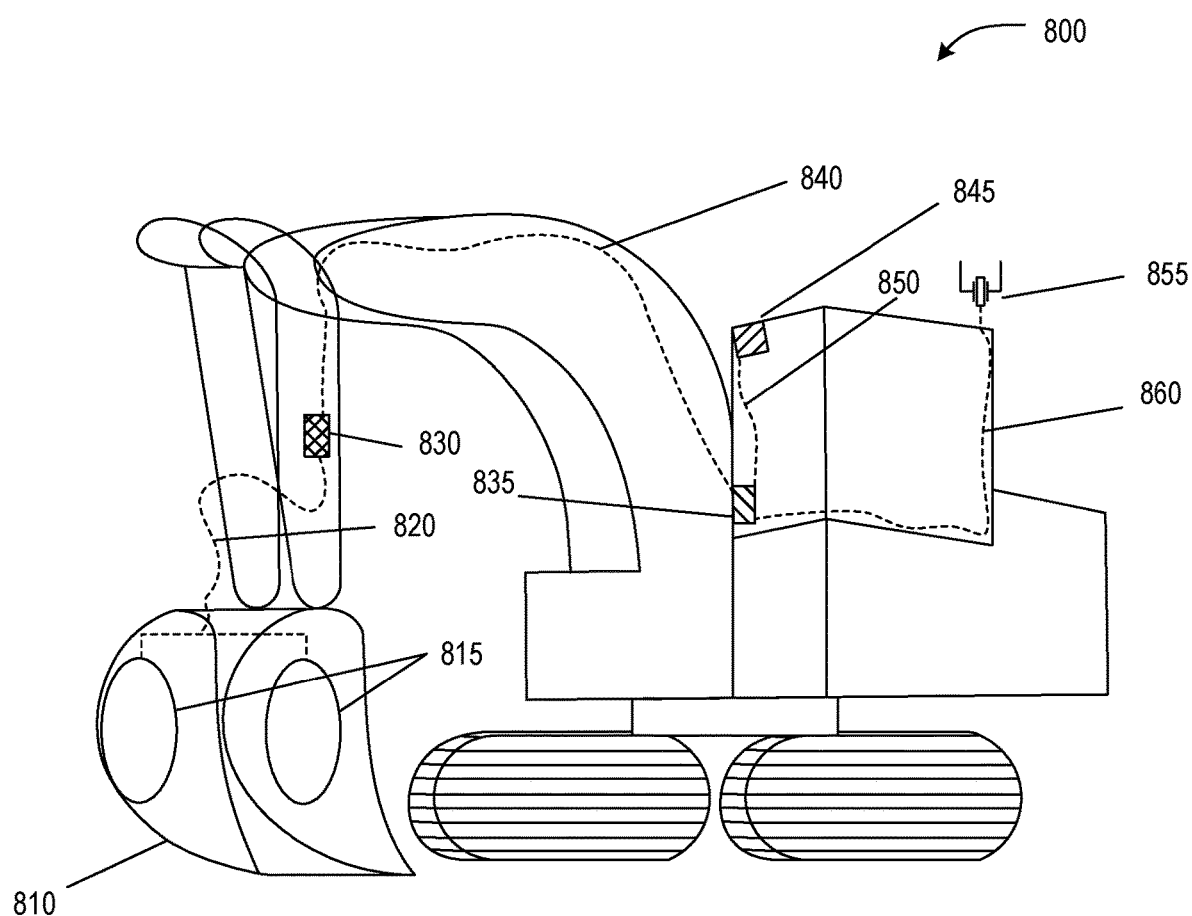
FIG. 8 illustrates one embodiment of a hydraulic mining shovel that may be used in methods and systems for extracting materials.

FIG. 8 illustrates one embodiment of a hydraulic mining shovel apparatus that may be used in methods and systems for extracting materials and mineral ores. FIG. 8 illustrates a typical hydraulic mining shovel arrangement indicating the installation of the sensors in the bucket, the control enclosure mounted on the hydraulic arm, and the industrially hardened computer, analog to digital converter and data/control signal output hardware mounted in the operator's cabin of the mining shovel. In some embodiments, only the sensors are interconnected to the bucket and the remaining equipment is communicably connected with the bucket, but not physically connected with the bucket or the mining shovel. A "bucket" such as element 810 in FIG. 8 includes, but is not limited to, rail cars, or any other container for hauling ore from a mine to, or between processes. In some embodiments, the bucket may be a part of the magnetic circuit created by the sensor coil. Thus, in some embodiments, the shovel is or becomes the sensor, or part of the sensor.

Referring now to the implementation of the system, in FIG. 8 there is shown an isometric view of a typical hydraulic mining shovel, with an arrangement indicating the installation of the sensors in the bucket, the control enclosure mounted on the hydraulic arm, and the industrially hardened computer, analog to digital converter, a decision support system which may include a human/machine interface for decision support and data/control signal output hardware mounted in the operator's cabin of the mining shovel. The mining shovel bucket 810 houses the sensing coils 815 in a tiled, opposed arrangement. The specific arrangement of the sensors in the bucket within and among the wear materials in the bucket allows for protection of and therefore use of sensitive coil arrangements in the high impact and wear environment of the shovel bucket. Further, the specific size and orientation of the sensors is unique to the particular bucket, and determined by the desired coverage of the shovel bucket volume by the combined fields of the coils in the array. The sensing coils 815 are connected via a cable 820 to the control enclosure 830 mounted on the boom of the shovel.

The control enclosure 830 comprises the arbitrary waveform generator, the bridge network and signal conditioning electronics, and a reference sensor. The control enclosure 830 is connected to the analog to digital converter and the industrially hardened computer 835, mounted in the operator's cabin by a cable 840. The decision support system 845 may be a user interface in the operator's cabin of mining shovel 800 and connected to the industrially hardened computer 835 via a cable 850. In alternative embodiments, decision support system 845 may be a user interface on a computer in an office at a mine or ore processing facility or an automated facility that sorts minerals by, for example, dumping rail cars into different piles or otherwise sorting different grades of ore. Materials or mineral ores with an elemental content above that of a pre-determined cutoff are detected by the sensor array. The presence of mineral ores of higher grade than the arbitrary cutoff is detected by the sensor array and the results are reported to the industrially hardened computer. In cases where diversion by means of the shovel or other embodiment such as a diverter on the belt conveyor is autonomous, diversion is automatically effected. In some embodiments, such as where diversion is to be effected by the shovel operator, instructions as to the destiny of the mineral ore sample in the bucket are given to the operator by the decision support system. Reject material below an arbitrary cutoff is identified by a numerical readout of the chemistry values and/or a color indicator (e.g., 'RED') indicating action to reject the material is to be taken. Low grade ore between arbitrary cutoffs is identified by a numerical readout of the chemistry values and/or a color indicator (e.g., 'BLUE') indicating action to divert the material to a second stage of treatment is to be taken. High grade ore above an arbitrary cutoff is identified by a numerical readout of the chemistry values as well as a color indicator (e.g., 'GREEN') indicating action to divert the material to a final treatment stage is to be taken. In some embodiments, only a color indicating an action is displayed. This simple binary information signals the operator of the shovel to place the contents of the current load in either the ACCEPT or REJECT stream, as appropriate. Alternatively, the display could provide a numerical or graphical indication of the actual average ore grade currently in the shovel, so that the operator of the shovel could make finer-grained decisions based on this information. The data/control signal output hardware 855 is mounted on the operator's cabin and connected to the industrially hardened computer 835 by a cable 860. Variations of the particular mining shovel provide equivalent methods of mounting the invention, and as such, the invention is not limited to one specific arrangement of mining shovel. Sensors thus emplaced can simply be used for telemetry alone, i.e., the provision of information as to chemical content of the materials or mineral ores. Sensors thus emplaced can also be used for decision support, i.e., the provision of information to support decisions to further treat or not to treat the material at all. Sensors thus emplaced can, in conjunction with a diversion system previously described, or by providing decision support to the operator as previously described, be used to sort the material or mineral ore by rejecting gangue constituents of low metallic content from the mineral ore stream either individually or in batches.

Figure 9:
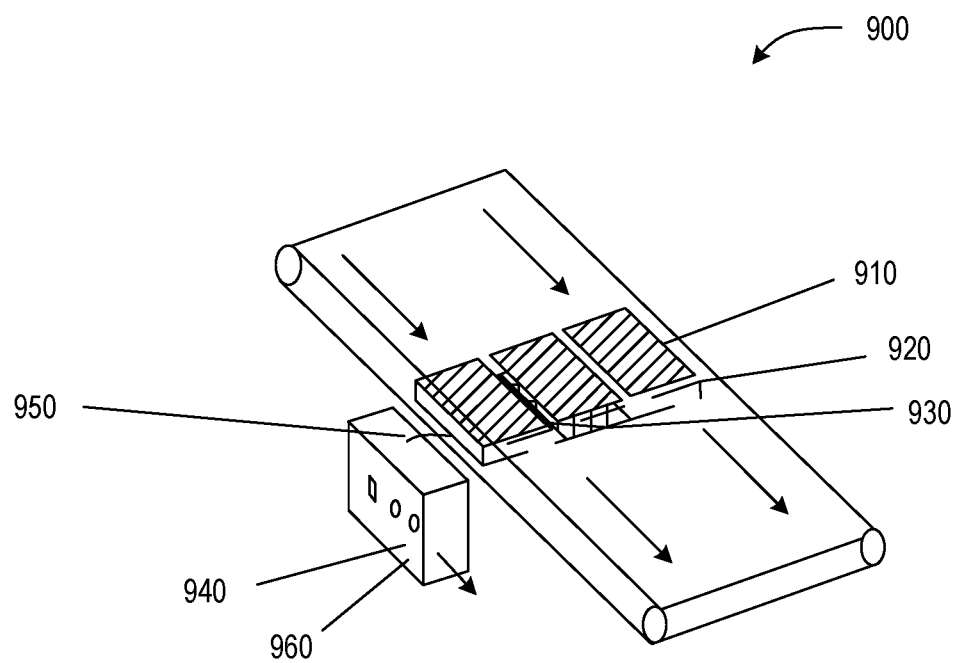
FIG. 9 illustrates one embodiment of a conveyor belt system that may be used in methods and systems for extracting minerals.

FIG. 9 illustrates one embodiment of a conveyor belt system 900 that may be used in methods and systems for extracting materials and mineral ores. FIG. 9 includes a control enclosure, electromagnetic sensors and sensor mounting chassis as mounted on a conveyor belt that may be used in sorting minerals. Referring now to the implementation of the system, in FIG. 9, an isometric view of the control enclosure 940, electromagnetic sensors 920 and sensor mounting chassis 910 as mounted under a conveyor belt. The sensor mounting chassis 910 carries the active sensors 920 and reference sensors 930 and the control enclosure 940. The control enclosure 940 comprises the waveform generator 950, the bridge network and signal conditioning electronics 960. Control enclosure 940 may also include the analog to digital converter, the industrially hardened computer, and the data and control output module. The sensor mounting chassis 910 is placed under the belt of a belt conveyor (not shown for clarity). Variations of the particular conveyor belt provide equivalent methods of mounting the invention, and as such, the invention is not limited to one specific arrangement of a belt conveyor system. Variations of the particular belt or other conveyance provide equivalent methods of mounting the invention, and as such, the invention is not limited to one specific arrangement of conveyor. Sensors thus emplaced can simply be used for telemetry alone, i.e., the provision of information as to chemical content of the materials or mineral ores. Sensors thus emplaced can also be used for decision support, i.e., the provision of information to support decisions to further treat or not to treat the material at all. Sensors thus emplaced can, in conjunction with a diversion system previously described, or by providing decision support to the operator as previously described, be used to sort the material or mineral ore by rejecting gangue constituents of low metallic content from the mineral ore stream either individually or in batches.

Figure 10:
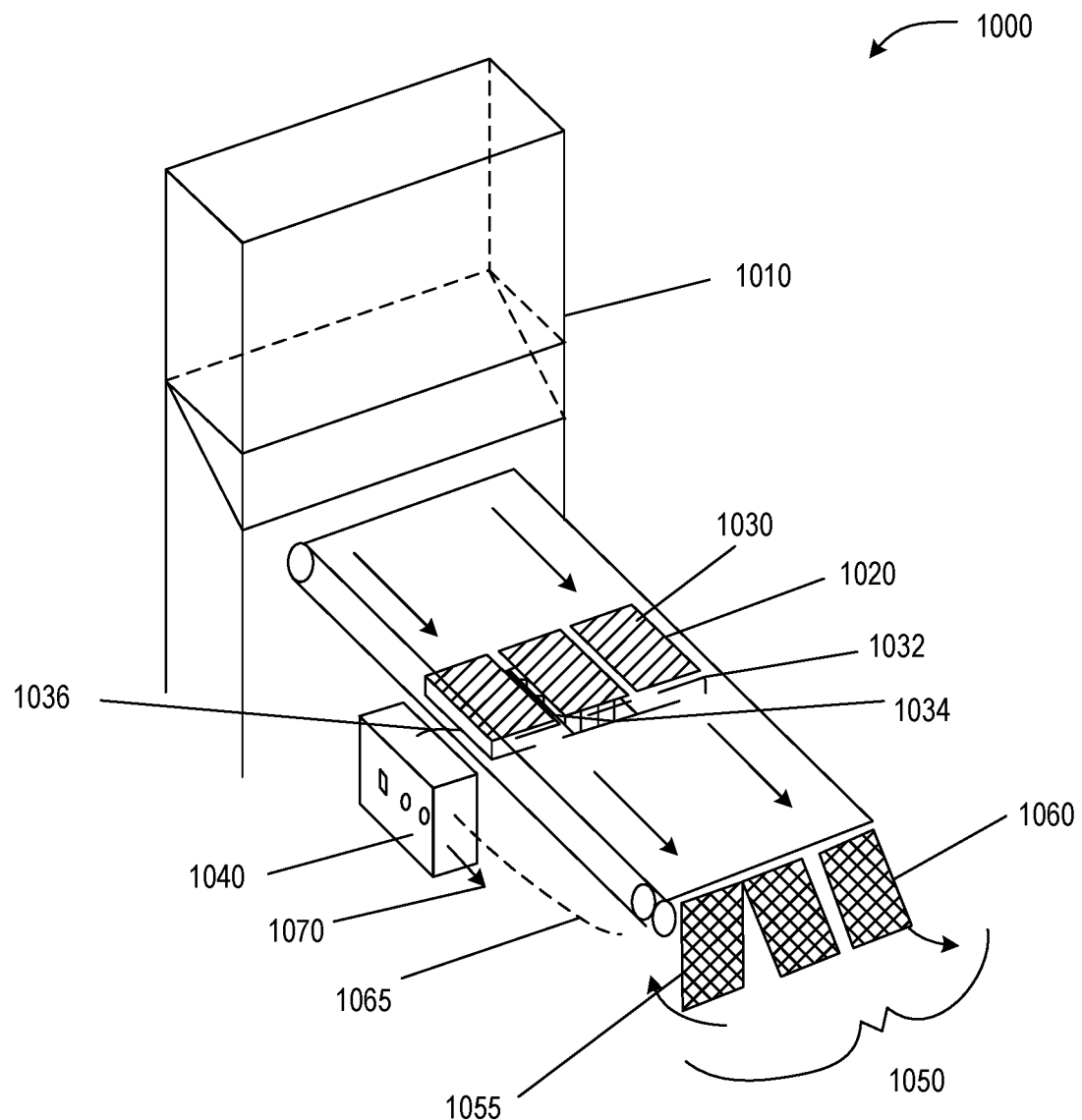
FIG. 10 illustrates an embodiment of a sorting system that may be used in methods and systems for extracting materials.

FIG. 10 illustrates an embodiment of a sorting system that may be used in methods and systems for extracting minerals. FIG. 10 includes a feed system 1010, control enclosure 1040, sensor mounting chassis 1030 with electromagnetic sensors 1032, reference sensor 1034, and sample rejection mechanism 1050 as mounted for example on a conveyor belt. The feed system 1010 contains the sample-set to be sorted and introduces the mineral sample individually onto the sensors 1032 in a controlled fashion. The sensor mounting chassis 1030 carries the active sensing coils 1032, reference sensor 1034 and the control enclosure 1040. The coils 1032 and 1034 are connected to the control enclosure 1040 by a cable 1036. The control enclosure 1040 comprises the waveform generator, the bridge network and signal electronics, the analog to digital converter, the industrially hardened computer, and the data and control output module. The control enclosure is connected to the sample rejection mechanism 1050 by means of a cable 1065. The sample rejection mechanism comprises an accept mechanism 1055 to accept a sample and a reject mechanism 1060 to reject a sample. The control enclosure transmits data from the electromagnetic sorter to other devices via a cable 1070. The electromagnetic sorter is placed, for example, under the belt of a belt conveyor. The response of the system to samples of known conductive or magnetic content has been determined as previously described. The actual content of metallic material as measured by chemical assay/testing is then correlated to the spectral output of the sensors. The actual content of similar material passing over the sensors can then be determined directly by the system and accepted or rejected accordingly. Variations of the particular methods of conveying provide equivalent methods of mounting the invention, and as such, the invention is not limited to one specific arrangement of conveyor.

Figure 11:
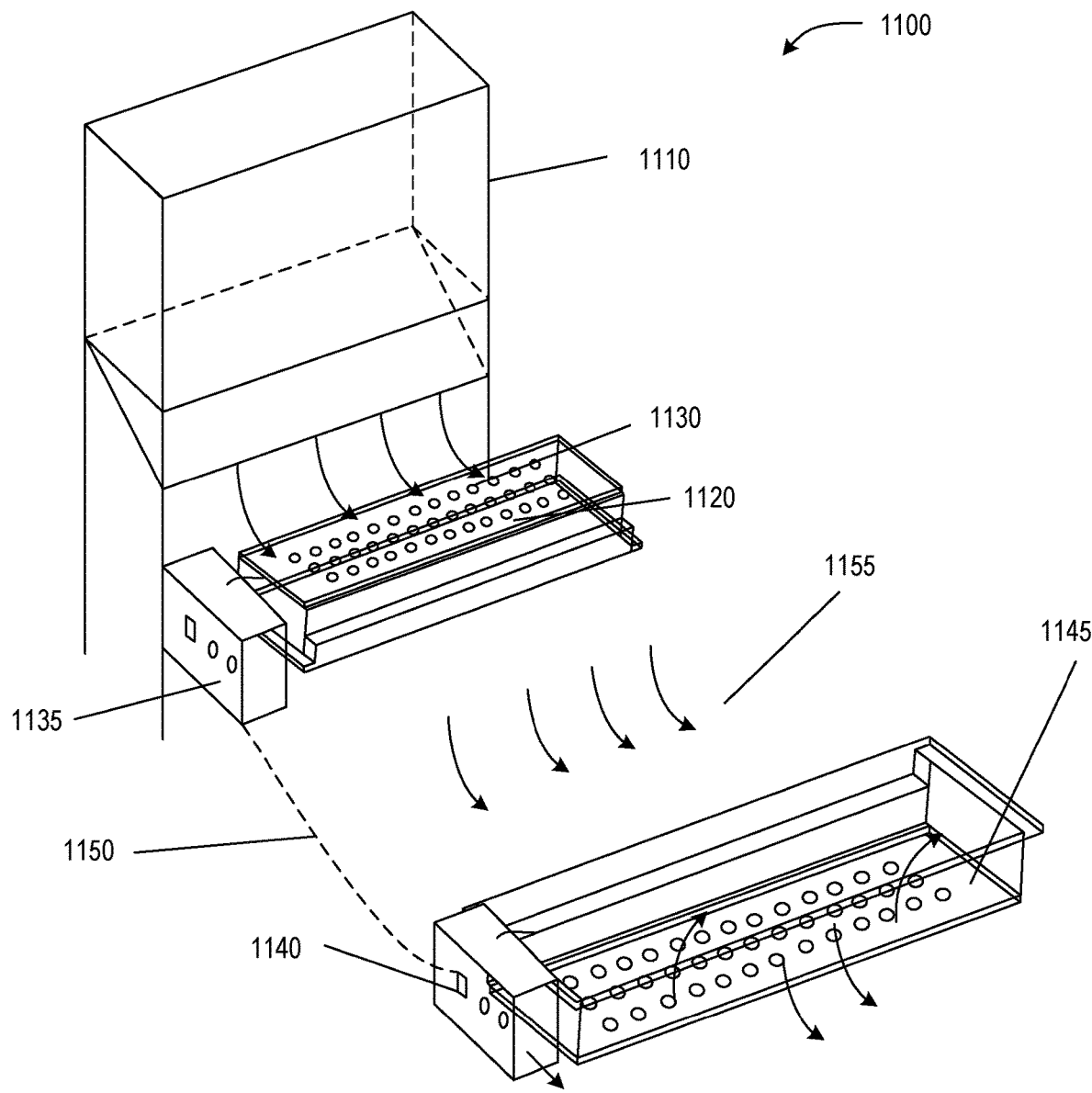
FIG. 11 illustrates an embodiment of a sorting system that may be used in methods and systems for extracting materials.

FIG. 11 illustrates an embodiment of a sorting system that may be used in methods and systems for extracting materials. The sorting system 1100 uses a multi-sensor array installed together with a multi-channel diversion system for the rejection of individual particles of low metallic content. More particularly, sorting system 1100 includes a feed system 1110, feed arrangement 1130, sensor mounting chassis with electromagnetic sensors 1120, industrially hardened computer 1135, cable 1150, transport mechanism 1155, and sample reject diversion mechanism 1145. In operation, samples of conductive or magnetic material either individually, or in batch mode are loaded into feed system 1110. The samples are exposed to the sensing coil array 1120 by the feed arrangement 1130. Electric currents are induced in conductive material passing through the sensing coil fields. These currents generate magnetic fields in respect of the conductive material, which in turn generate counter-currents in the coil, changing the impedance of the coil-conductor system as seen across the coil. Magnetic material passing through or present within the sensor field alters the impedance of the coil, altering the current passing through the coil. The change in impedance of each coil in turn is read, analyzed and stored by the analog to digital converter and industrially hardened computer 1135. The response of the system to samples of known conductive or magnetic content has been determined as previously described. The actual content of metallic material as measured by chemical assay is then correlated to the spectral output of the sensors. The actual content of similar material passing over the sensors can then be determined directly by the system.

The response of each individual coil in the array to the conductive or magnetic content in the sample is compared to a user-defined value stored in the industrially hardened computer. For material above a certain conductive or magnetic content, an 'accept' signal is generated by the industrially hardened computer. For material below a certain conductive or magnetic content, a 'reject' signal is generated by the industrially hardened computer 1135. Signals from the industrially hardened computer 1135 are transmitted to the multi-channel diverter mechanism control station 1140 via cable 1150. The samples are transported to the sample rejection diversion mechanism via transport mechanism 1155. For coil n with a 'reject' signal, a divert instruction is given to diverter n in the sample reject diversion mechanism 1145 and the sample is rejected. Samples can be rejected either individually or in batch mode as the case may be. Other equivalent arrangements are easily conceivable, and the invention is not limited to the above described arrangement.

FIG. 12 illustrates a sensor array layout that may be used in various embodiments of the present invention. As discussed, multiple arrays of coils can be used, with each array having one or more sensing coils and at least one reference coil. Each individual coil may be stimulated individually, and each sensing coil collects information about the ore. The output of each sensor is channelized, and the channelized sensor information can be used to correlate a difference between the output from the multiple sensors to effectively spatially separate the ore. Thus, the multiple sensor array provides a more granular output than prior art systems, with faster processing speed than in prior systems.

CONCLUSION

As explained above, aspects of the invention can be embodied in a special purpose computer or data processor that is specifically programmed, configured, or constructed to perform one or more of the computer-executable instructions explained in detail herein. While aspects of the invention, such as certain functions, are described as being performed exclusively on a single device, the invention can also be practiced in distributed environments where functions or modules are shared among disparate processing devices, which are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the invention may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme).

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." A mining apparatus is used herein to refer to any mining equipment such as but not limited to, excavators, loaders, draglines, hydraulic shovels, electric wire-rope shovels, scooptrams, backhoes and the like. Other embodiments such as belt conveyors, belt feeders, vibrating pan feeders, apron feeders, ore passes, ore chutes, ore bins, and ore sorting machines are also possible.

As used herein, the terms "connected," "coupled," or any variant thereof means any connection or coupling, either direct or indirect, between two or more elements; the coupling or connection between the elements can be physical, logical, or a combination thereof. As used herein, "substantially in real time" refers to the amount of time a computing device takes to exchange electrical communications and/or process and/or compute data. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. For example, while only one aspect of the invention is recited as a means-plus-function claim under 35 U.S.C § 112, sixth paragraph, other aspects may likewise be embodied as a means-plus-function claim, or in other forms, such as being embodied in a computer-readable medium. (Any claims intended to be treated under 35 U.S.C. § 112, ¶ 6 will begin with the words "means for", but use of the term "for" in any other context is not intended to invoke treatment under 35 U.S.C. § 112, ¶ 6.) Accordingly, the applicant reserves the right to pursue additional claims after filing this application to pursue such additional claim forms, in either this application or in a continuing application.

We claim:

1. A conveyor belt system comprising:
    a conveyor belt configured to transport ore comprising one or more minerals;
    an electromagnetic sensor system associated with the conveyor belt for collecting data related to the ore,
        the electromagnetic sensor system comprising at least one active sensor and
        configured to:
            generate source signals,
            apply the source signals to the at least one active sensor, and
            collect, while the source signals are being applied, a response to the source signals from the at least one active sensor in the presence of the ore; and
    a data analysis system communicatively coupled to the electromagnetic sensor system and configured to:

compare the response of the at least one active sensor in the presence of the ore to the response of at least one reference sensor not in the presence of the ore, and analyze the data to determine a content of the one or more minerals in the ore; and a decision support system coupled to the data analysis system configured to provide an output related to sorting and processing ore in response to the content of the one or more minerals.

2. The conveyor belt system of claim 1, wherein each of the at least one active sensors comprises:
a coil wound from signal wire,
an upper electrostatic shield,
a lower electrostatic shield,
a molded casing, and
a shielded signal cable connecting the coil to a bridge network.

3. The conveyor belt system of claim 1, wherein each of the at least one reference sensors comprises:
a coil wound from signal wire,
an upper electrostatic shield,
a lower electrostatic shield,
a molded casing, and
a shielded signal cable connecting the coil to a bridge network.

4. The conveyor belt system of claim 1, wherein the content of the one or more minerals comprises at least one of: composition, grade, conductivity, or magnetic susceptibility, and wherein the data analysis system is further configured to:
compare the data with previously recorded data associated with minerals of known content, and
determine the content of the one or more minerals based on the comparison.

5. The conveyor belt system of claim 1, wherein the source signals are generated using an arbitrary waveform generator,
wherein the electromagnetic sensor system is further configured to:
apply the source signals to the at least one reference sensor, and
collect a response to the source signals from the at least one reference sensor,
wherein the response to the source signals comprises impedance, and
wherein the impedance of the at least one active sensor is compared to the impedance of the at least one reference sensor.

6. The conveyor belt system of claim 4, wherein the data analysis system is further configured to:

calculate an impedance value based on a difference between the impedance of the at least one active sensor and the impedance of the at least one reference sensor; and calculate a value representing a quantity of conductive and magnetic material in the ore based on the impedance value.

7. The conveyor belt system of claim 1, wherein the sensor system is coupled to a computing device, and wherein the electromagnetic sensor system is controlled by the computing device.

8. The conveyor belt system of claim 1, wherein the electromagnetic sensor system is disposed under the conveyor belt.

9. The conveyor belt system of claim 1, wherein the data analysis system is further configured to:
determine a quantity of conductive and magnetic material in the ore based on a difference between an impedance of the at least one active sensor and an impedance of the at least one reference sensor.

10. A conveyor belt system comprising:
a conveyor belt configured to transport ore comprising one or more minerals;
an electromagnetic sensor system associated with the conveyor belt for collecting data related to the ore,
wherein the electromagnetic sensor system comprises at least one active sensor, and
wherein the electromagnetic sensor system:
generates source signals,
applies the source signals to the at least one active sensor, and
collects, while the source signals are being applied, a response to the source signals from the at least one active sensor in the presence of the ore; and
a data analysis system communicatively coupled to the electromagnetic sensor system, wherein the data analysis system:
compares the response of the at least one active sensor in the presence of the ore to the response of at least one reference sensor not in the presence of the ore, and
analyzes the data to determine a content of the one or more minerals in the ore; and
a decision support system coupled to the data analysis system, wherein the decision support system provides an output related to sorting and processing ore in response to the content of the one or more minerals.

11. The conveyor belt system of claim 1, wherein the data analysis system:
determines a quantity of conductive and magnetic material in the ore based on a difference between an impedance of the at least one active sensor and an impedance of the at least one reference sensor.

* * * * *